(12) United States Patent
Rudolph et al.

(10) Patent No.: US 8,871,230 B2
(45) Date of Patent: Oct. 28, 2014

(54) CONJUGATE WITH TARGET-FINDING LIGAND AND USE THEREOF

(75) Inventors: Carsten Rudolph, München (DE); Johannes-Peter Geiger, München (DE)

(73) Assignee: ethris GmbH, Martinsried (DE)

( * ) Notice: Subject to any disclaimer, the term of this patent is extended or adjusted under 35 U.S.C. 154(b) by 0 days.

(21) Appl. No.: 13/518,318

(22) PCT Filed: Dec. 21, 2010

(86) PCT No.: PCT/EP2010/007846
§ 371 (c)(1),
(2), (4) Date: Sep. 5, 2012

(87) PCT Pub. No.: WO2011/076391
PCT Pub. Date: Jun. 30, 2011

(65) Prior Publication Data
US 2012/0328520 A1   Dec. 27, 2012

(30) Foreign Application Priority Data

Dec. 21, 2009   (EP) .................................... 09015812

(51) Int. Cl.
| | | |
|---|---|---|
| *A61K 9/00* | (2006.01) | |
| *A61K 9/14* | (2006.01) | |
| *A61K 47/48* | (2006.01) | |
| *C12N 15/88* | (2006.01) | |

(52) U.S. Cl.
CPC ..... *A61K 47/48192* (2013.01); *A61K 47/48092* (2013.01); *A61K 47/48284* (2013.01); *C12N 15/88* (2013.01)
USPC ...................... 424/400; 400/178.1; 400/184.1

(58) Field of Classification Search
USPC ..................... 424/400, 178.1, 184.1
See application file for complete search history.

(56) References Cited

U.S. PATENT DOCUMENTS

| | | | | |
|---|---|---|---|---|
| 2006/0147520 | A1* | 7/2006 | Ruegg ........................... | 424/464 |
| 2006/0217293 | A1* | 9/2006 | Orlando et al. ................. | 514/8 |
| 2012/0010145 | A1* | 1/2012 | Guarnieri ...................... | 514/15.5 |
| 2012/0177693 | A1* | 7/2012 | Cipolla et al. ................. | 424/400 |

FOREIGN PATENT DOCUMENTS

| | | |
|---|---|---|
| AU | 2010335528 | 7/2012 |
| CA | 2784705 | 6/2011 |
| CN | 102770161 | 11/2012 |
| EA | 201200919 | 2/2013 |
| EP | 2338520 | 6/2011 |
| EP | 2515945 | 10/2012 |
| JP | 2013515023 | 5/2013 |
| KR | 20120103725 | 9/2012 |
| WO | WO 03/074088 | 9/2003 |
| WO | WO 2011/076391 | 6/2011 |

OTHER PUBLICATIONS

Hirsh et al., J. Clinical Oncology, vol. 23, No. 14 (May 10, 2005).*
Elfinger et al., J. Controlled Release, 135 (2009), 234-241 (Available online Jan. 24, 2009).*
Nakae et al., J Pharmacology and Experimental Therapeutics, vol. 315, No. 3, 1136-1142, 1136 (2005).*
Alton EW, et al. Cationic lipid-mediated CFTR gene transfer to the lungs and nose of patients with cystic fibrosis: a double-blind placebo-controlled trial. Lancet. Mar. 20, 1999; 353 (9157): 947-54.
Ayer LM, et al. 4,5-Dihydro-1H-imidazol-2-yl)-[4-(4-isopropoxybenzyl)-phenyl]-amine (RO1138452) is a selective, pseudo-irreversible orthosteric antagonist at the prostacyclin (IP)-receptor expressed by human airway epithelial cells: IP-receptor-mediated inhibition of CXCL9 and CXCL10 release. J. Pharmacol. Exp. Ther. Feb. 2008; 324 (2): 815-26.
Blessing T, et al. Different strategies for formation of pegylated EGF-conjugated PEI/DNA complexes for targeted gene delivery. Bioconjug. Chem. Jul.-Aug. 2001; 12 (4): 529-37.
Bley KR, et al. RO1138452 and RO3244794: characterization of structurally distinct, potent and selective IP (prostacyclin) receptor antagonists. Br. J. Pharmacol. Feb. 2006; 147 (3): 335-45.
Boie Y, et al. Cloning and expression of a cDNA for the human prostanoid IP receptor. J. Biol. Chem. Apr. 22, 1994; 269 (16): 12173-8.
Boussif O, et al. A versatile vector for gene and oligonucleotide transfer into cells in culture and in vivo: polyethylenimine. Proc. Natl. Acad. Sci. U S A. Aug. 1, 1995; 92(16): 7297-301.
Buckley SM, et al. Luciferin detection after intranasal vector delivery is improved by intranasal rather than intraperitoneal luciferin administration. Hum. Gene Ther. Oct. 2008; 19 (10): 1050-6.
Canonico AE, et al. Aerosol and intravenous transfection of human alpha 1-antitrypsin gene to lungs of rabbits. Am. J. Respir. Cell Mol. Biol. Jan. 1994; 10 (1): 24-9.
Chul Cho K, et al. Folate receptor-mediated intracellular delivery of recombinant caspase-3 for inducing apoptosis. J. Control. Release. Nov. 2, 2005; 108 (1): 121-31.
Clark RB, et al. Partial agonists and G protein-coupled receptor desensitization. Trends Pharmacol. Sci. Jul. 1999; 20 (7): 279-86.
Clark RD, et al. Discovery and SAR development of 2-(phenylamino) imidazolines as prostacyclin receptor antagonists [corrected]. Bioorg. Med. Chem. Lett. Feb. 23, 2004; 14 (4): 1053-6.
Coleman RA, et al. International Union of Pharmacology classification of prostanoid receptors: properties, distribution, and structure of the receptors and their subtypes. Pharmacol. Rev. Jun. 1994; 46 (2): 205-29.
Davies L, et al. Plasmid inhalation: delivery to the airways; 2005 (21 pages).
Dunlap DD, et al. Nanoscopic structure of DNA condensed for gene delivery. Nucleic Acids Res. Aug. 1, 1997; 25 (15): 3095-101.

(Continued)

*Primary Examiner* — Michael G Hartley
*Assistant Examiner* — Robert Cabral
(74) *Attorney, Agent, or Firm* — Ballard Spahr LLP

(57) ABSTRACT

Described is a conjugate of agent complex and at least one target-finding ligand, where the agent complex comprises an agent encapsulated by an encapsulation material and where the target-finding ligand is a prostacyclin analog, and the use of the conjugate.

14 Claims, 9 Drawing Sheets

(56) References Cited

OTHER PUBLICATIONS

Figure 1:
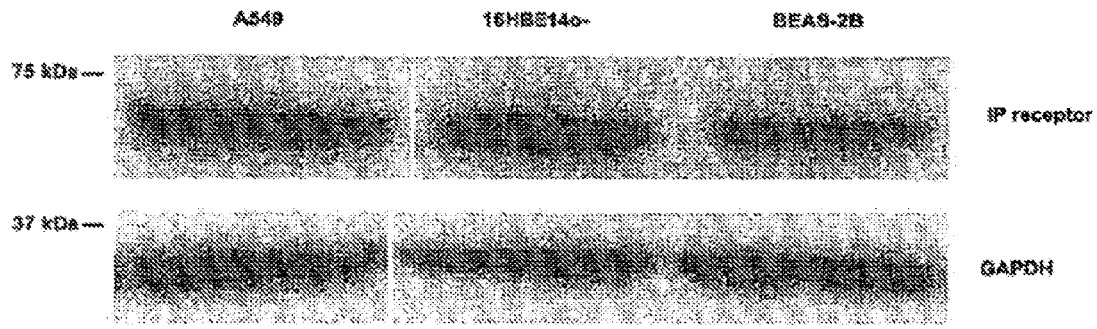

Elfinger M, et al. Characterization of lactoferrin as a targeting ligand for nonviral gene delivery to airway epithelial cells. Biomaterials. Aug. 2007; 28 (23): 3448-55.

Elfinger M, et al. Targeting of the beta(2)-adrenoceptor increases nonviral gene delivery to pulmonary epithelial cells in vitro and lungs in vivo. J. Control. Release. May 5, 2009; 135 (3): 234-41.

Ferguson SS. Evolving concepts in G protein-coupled receptor endocytosis: the role in receptor desensitization and signaling. Pharmacol. Rev. Mar. 2001; 53 (1): 1-24.

Gautam A, et al. Pulmonary cytokine responses associated with PEI-DNA aerosol gene therapy. Gene Ther. Feb. 2001; 8 (3): 254-7.

Geiger J, et al. Targeting of the prostacyclin specific IP1 receptor in lungs with molecular conjugates comprising prostaglandin I2 analogues. Biomaterials. Apr. 2010; 31 (10): 2903-11.

Geiger J, et al. Vectors for pulmonary gene therapy. Int J Pharm. May 5, 2010; 390 (1): 84-8.

Gill DR, et al. The development of gene therapy for diseases of the lung. Cell Mol. Life Sci. Feb. 2004; 61 (3): 355-68.

Giovanazzi S, et al. Internalization and down-regulation of the prostacyclin receptor in human platelets. Biochem. J. Jul. 1, 1997; 325 ( Pt 1): 71-7.

Gurunathan S, et al. DNA vaccines: immunology, application, and optimization. Annu Rev. Immunol. 2000; 18: 927-74.

Huth S, et al. Insights into the mechanism of magnetofection using PEI-based magnetofectins for gene transfer. J. Gene Med. Aug. 2004; 6 (8): 923-36.

Huth S, et al. Interaction of polyamine gene vectors with RNA leads to the dissociation of plasmid DNA-carrier complexes. J. Gene Med. Dec. 2006; 8 (12): 1416-24.

Hyde SC, et al. CpG-free plasmids confer reduced inflammation and sustained pulmonary gene expression. Nat. Biotechnol. May 2008; 26 (5): 549-51.

Kircheis R, et al. Coupling of cell-binding ligands to polyethylenimine for targeted gene delivery. Gene Ther. May 1997; 4 (5): 409-18.

Krug S, et al. Inhaled iloprost for the control of pulmonary hypertension. Vasc. Health Risk Manag. 2009; 5 (1): 465-74.

McLachlan G, et al. Optimizing aerosol gene delivery and expression in the ovine lung. Mol. Ther. Feb. 2007; 15 (2): 348-54.

Namba T, et al. cDNA cloning of a mouse prostacyclin receptor. Multiple signaling pathways and expression in thymic medulla. J. Biol. Chem. Apr. 1, 1994; 269 (13): 9986-92.

Narumiya S, et al. Prostanoid receptors: structures, properties, and functions. Physiol. Rev. Oct. 1999; 79 (4): 1193-226.

Olschewski H, et al. Prostacyclin and its analogues in the treatment of pulmonary hypertension. Pharmacol. Ther. May 2004; 102 (2): 139-53.

Rejman J, et al. Size-dependent internalization of particles via the pathways of clathrin-and caveolae-mediated endocytosis. Biochem. J. Jan. 1, 2004; 377 (Pt 1): 159-69.

Rudolph C, et al. Jet nebulization of PEI/DNA polyplexes: physical stability and in vitro gene delivery efficiency. J. Gene Med. Jan.-Feb. 2002; 4 (1): 66-74.

Rudolph C, et al. Aerosolized nanogram quantities of plasmid DNA mediate highly efficient gene delivery to mouse airway epithelium. Mol. Ther. Sep. 2005; 12 (3): 493-501.

Rudolph C, et al. Methodological optimization of polyethylenimine (PEI)-based gene delivery to the lungs of mice via aerosol application. J. Gene Med. Jan. 2005; 7 (1): 59-66.

Skoro-Sajer N, et al. Treprostinil for the treatment of pulmonary hypertension. Expert Opin. Pharmacother. Jun. 2008; 9 (8): 1415-20.

Smyth EM, et al. Internalization and sequestration of the human prostacyclin receptor. J. Biol. Chem. Oct. 13, 2000; 275 (41): 32037-45.

Snyder SL, et al. An improved 2,4,6-trinitrobenzenesulfonic acid method for the determination of amines. Anal. Biochem. Mar. 1975; 64 (1): 284-8.

Stitham J, et al. Human prostacyclin receptor structure and function from naturally-occurring and synthetic mutations. Prostaglandins Other Lipid Mediat. Jan. 2007; 82 (1-4): 95-108.

Strauss WL, et al. Prostanoid therapy for pulmonary arterial hypertension. Clin. Chest. Med. Mar. 2007; 28 (1): 127-42.

Ungaro F, et al. Spectrophotometric determination of polyethylenimine in the presence of an oligonucleotide for the characterization of controlled release formulations. J. Pharm. Biomed. Anal. Feb. 5, 2003; 31 (1): 143-9.

Zhang Z, et al. Glycosylation of the human prostacyclin receptor: role in ligand binding and signal transduction. Mol. Pharmacol. Sep. 2001; 60 (3): 480-7.

International Search Report issued Feb. 22, 2011 by the International Searching Authority for PCT/EP2010/007846 filed Dec. 21, 2010 published as WO 2011/076391 [Inventor—Rudolph; Applicant—Ethris GmbH] [7 pages].

International Preliminary Report on Patentability and Written Opinion issued Jun. 26, 2012 by the International Bureau for PCT/EP2010/007846 filed Dec. 21, 2010 published as WO 2011/076391 [Inventor—Rudolph; Applicant—Ethris GmbH] [24 pages].

European Search Report issued Apr. 20, 2010 by the European Patent Office for European Application No. EP 09015812.2 filed Dec. 21, 2009 published as EP 2338520 [Inventor—Rudolph; Applicant—Univ Munich L Maximilians] [8 pages] [no translation available].

* cited by examiner

A

B

Table 1

|  | N/P 2 | N/P 3 | N/P 4 | N/P 5 | N/P 6 | N/P 8 |
|---|---|---|---|---|---|---|
| PEI | 1258±787 (0.34±0.04) | 69±11 (0.15±0.03) | 61±10 (0.17±0.01) | 60±11 (0.19±0.02) | 53±8 (0.16±0.05) | 51±3 (0.14±0.01) |
| $F_{ILO}=2$ | 1197±1729 (0.37±0.23) | 804±804 (0.25±0.13) | 97±20 (0.17±0.07) | 77±19 (0.15±0.03) | 73±17 (0.15±0.06) | 70±17 (0.16±0.05) |
| $F_{ILO}=5$ | 149±16 (0.17±0.04) | 169±35 (0.10±0.02) | 82±4 (0.11±0.03) | 75±15 (0.13±0.02) | 74±11 (0.13±0.01) | 76±16 (0.14±0.04) |
| $F_{ILO}=8$ | 207±137 (0.19±0.10) | 366±31 (0.25±0.06) | 261±13 (0.12±0.03) | 165±43 (0.08±0.04) | 106±7 (0.08±0.01) | 87±12 (0.12±0.03) |
| $F_{ILO}=16$ | 141±26 (0.18±0.02) | 292±73 (0.22±0.05) | 2314±946 (0.26±0.14) | 418±156 (0.17±0.13) | 258±61 (0.12±0.03) | 213±48 (0.08±0.02) |

CONJUGATE WITH TARGET-FINDING LIGAND AND USE THEREOF

CROSS REFERENCE TO RELATED APPLICATIONS

The present application is a National Phase Application of International Application No. PCT/EP2010/007846, filed Dec. 21, 2010, which claims priority to European Patent Application No. 09015812.2, filed Dec. 21, 2009, which applications are incorporated herein fully by this reference.

The invention relates to conjugates comprising an agent which include a prostacyclin analog as target-finding structure, and to the use of such conjugates for gene therapy and/or for gene transfer in bronchial and alveolar epithelial cells.

The lungs are, firstly, an organ whose function is vital and, secondly, the lungs are an organ which, owing to its large surface area and accessibility, is attractive for introducing active substances or active agents into the body.

It has long been known to introduce active agents into the lungs via aerosols, nebulizers, inhalers or pump sprays, both for a local and for a systemic activity. It is also known to administer viral or nonviral gene transfer agents via the lungs for gene therapy purposes. The use of both viral and nonviral excipients frequently brings about side-effects. This is due in particular to the fact that the dose must be relatively high since the gene transfer, i.e. the introduction of the desired genes into cells, is frequently not sufficiently effective. Researchers have, therefore, looked for a long time for agents with which to improve gene transfer efficacy. In this context, it has already been proposed to encapsulate genes with a cationic lipid, since cationic particles are phagocyted more easily. An agent which has been proposed in this context and which is already the subject of clinical tests [7] is Genzyme Lipid 67. It is also known to use polyethyleneimine polymers (PEI) for encapsulating nucleic acids [8]. Although PEI is capable of protecting DNA, it has the disadvantage that the gene transfer efficacy is poor, and it has also been found that the high dose of PEI, which is required due to the poor transfection efficacy, causes inflammations.

Researchers have therefore also attempted for a long time to provide cationic-polymer-encapsulated particles with ligands intended to introduce the particles into cells. Attempts have already been made using transferrin [10], folic acid [11], lactoferrin [12], clenbuterol [13] and growth factors such as EGF [14]. Although it was possible to improve the PEI-mediated gene transfer with these ligands, there is still a demand for delivering active agents to the lungs in a targeted manner and with high efficiency.

Furthermore, there are ongoing attempts to find novel routes for the therapeutic treatment of chronic pulmonary diseases, for which gene transfer is a promising approach. Pulmonary diseases which are due to hereditary or acquired protein and/or gene defects could be improved, alleviated or indeed cured by providing the missing or damaged proteins or gene products. However, the administration for such a purpose must be regular. Therefore, a balance must be found between undesired side-effects and desired therapeutic effect. Another important aspect is the dose frequency required for a prolonged therapy.

It was therefore an object of the invention to provide conjugates which allow active substances or active agents which are suitable for the treatment or alleviation of pulmonary diseases to be provided in a form which can be taken up in a targeted manner by lung cells, in particular by bronchial and alveolar epithelial cells.

This object is solved with a conjugate as defined in claim 1.

Surprisingly, it has been found that pulmonary epithelial cells, i.e. bronchial epithelial cells and alveolar epithelial cells, have $IP_1$ receptors and that these receptors may be targeted for an efficient transfer of active-substance-comprising particles. Using the conjugates according to the invention, epithelial cells in the bronchi and in the alveoli may successfully be targeted via these $IP_1$ receptors, by using at least one prostacyclin analog as the target-finding structure.

In what follows, the subject matter of the invention is described in detail, and the characteristics and advantages are illustrated in greater detail. The invention is also illustrated in greater detail in the adjoined figures, in which FIG. 1 shows the results of a Western Blot analysis of the $IP_1$ receptor expression in human alveolar and bronchial epithelial cells.

FIG. 2 shows the fluorescence intensity of A549 and 16HBE14o-cells following incubation with FLUO-BSA-ILO and FLUO-BSA-TRP, respectively.

FIG. 3*a* shows the fluorescence intensity of FLUO-BSA in comparison with FLUO-BSA-ILO in different cell lines; FIG. 3*b* and FIG. 3*c* show the mean fluorescence intensities upon increasing CAY10449 and ILO concentrations, respectively; FIG. 3*d* shows the mean fluorescence intensity of FLUO-BSA-ILO after the addition of CAY10449; FIG. 3*e* shows confocal laser scanning micrographs of the surface binding.

FIG. 4 shows the DNA release for PEI-g-ILO constructs with different N/P ratios.

FIG. 5*a* shows the degree of expression for cells transfected with PEI-g-ILO gene vectors in comparison with unmodified PEI; FIG. 5*b* shows the gene expression for PEI-g-ILO in comparison with PEI; FIG. 5*c* shows the degrees of expression for PEI-g-ILO in A549 and BEAS-2B cells in comparison with PEI.

FIG. 6*a* shows in-vivo studies of the gene expression of luciferase; FIG. 6*b* shows the luciferase expression in homogenized pulmonary tissue obtained from mice which had received PEI-g-ILO $F_{ILO}$=5 gene vectors in comparison with PEI gene vectors.

FIG. 7*a* shows the metabolic activity of untreated cells in comparison with cells treated with PEI or with construct according to the invention; FIG. 7*b* shows the change in the cytokine level following the administration of PEI or construct according to the invention in comparison with untreated cells.

FIG. 8 shows the dose-dependent gene vector delivery into pulmonary cells.

FIG. 9 shows the physical characterization of PEI/pCMV-luc and PEI-g-ILO/pCMV-luc gene vectors using PEI-g-11.-0 with different degrees of coupling ($F_{ILO}$=2, 5, 8, 16) at different N/P ratios: Measurements of the particle size and the polydispersity (in parentheses). The results are shown as the mean±standard deviation (n=3).

Surprisingly, it has been found that conjugates which include prostacyclin analogs as the target-finding structure are suitable for targeting epithelial cells in the lungs, in particular bronchial and alveolar cells, and are capable of introducing agents into the cells in a highly effective manner. Herewith there is now provided in accordance with the invention an agent for introducing active ingredients into pulmonary epithelial cells. This offers novel possibilities in the therapeutic treatment of a wide range of pulmonary diseases.

Prostacyclin belongs to the class of the prostaglandins and is known as prostaglandin $I_2$ or $PGI_2$; it targets and binds to the prostacyclin ($IP_1$) receptor. The $IP_1$ receptor is a 7-transmembrane-G-protein-coupled receptor which has been found predominantly on endothelial cells, in particular on muscle cells, for example on muscle cells of blood vessels [15-17]. The binding of prostacyclin to an $IP_1$ receptor agonist leads to an endosomal internalization of receptor/ligand complexes via clathrin-mediated processes [18, 19]. The inventors of the present invention have now found that this effect can be exploited for improving the targeted transfer of active agents into alveolar and bronchial epithelial cells and for making possible the uptake of active agents which are beneficial for the lungs or which treat pulmonary conditions.

In accordance with the invention, there is therefore provided a conjugate which includes at least one prostacyclin analog as targeting structure for bronchial and alveolar epithelial cells. Prostacyclin itself is too unstable and is degraded too quickly to be able to be used for the intended purpose. However, there are known stable prostacyclin analogs which likewise bind to the $IP_1$ receptor and act as agonists. In the present context, a prostacyclin analog means a compound which is derived from prostanoic acid, which has an ability to bind to the $IP_1$ receptor which is comparable to, or higher than, that of prostacyclin and which is more stable than natural prostacyclin. Compounds of this type are known. The known prostacyclin analogs are suitable for the conjugates according to the invention.

The ligands which are used by preference are iloprost and/or treprostinil, two prostacyclin analogs which are approved as pharmaceuticals. Other prostacyclin analogs may likewise be used.

A prostacyclin analog suitable for the invention is one that is more stable in a physiological environment and/or during storage than the naturally occurring prostacyclin. As specified hereinabove, prostacyclin is degraded very rapidly; it has a half-life of only a few minutes in a physiological environment, i.e. in the blood, and cannot be stored over a prolonged period. Prostacyclin analogs which are suitable for the invention are, therefore, those which retain their properties for at least 20 minutes, preferably for at least 30 minutes, even more preferably for at least 45 minutes in a physiological environment without being degraded or inactivated, or those which have a half-life of at least 15 minutes, preferably of at least 20 minutes, more preferably of at least 25 minutes, in a physiological environment. In the present context, the half-life is generally understood as being the period of time within which half of the starting material—in the present case the prostacyclin analog—has decomposed or has been inactivated or converted in a physiological environment. The half-life can be determined simply in the customary manner, for example by placing the prostacyclin analog in question into a physiological solution at a temperature of 35-37° C. and the amount of undecomposed prostacyclin is determined at the beginning and after predetermined periods.

A prostacyclin analog which is suitable for the invention is furthermore one that has the ability to bind to the $IP_1$ receptor which is comparable to, or higher than, that of prostacyclin. A method of determining the binding ability of a prostacyclin analog is a competitive method in which prostacyclin or a known prostacyclin analog such as iloprost and/or treprostinil and a prostacyclin analog candidate are conjugated with fluorescein and bovine serum albumin (BSA) and then added to various pulmonary cell lines, whereupon the binding and the cellular uptake are studied by flow cytometry and confocal laser scanning microscopy. A candidate which binds equally to or more than prostacyclin or iloprost or treprostinil is likewise preferred as part of the conjugate according to the invention. Equal binding ability means that the fluorescein-labeled candidate binds at least to the same extent as fluorescein-labeled prostacyclin or fluorescein-labeled iloprost or fluorescein-labeled treprostinil. If the proportion of fluorescein-labeled candidates is lower, this means that prostacyclin or iloprost or treprostinil displace the candidate from the binding so that the binding ability of the latter is not as great.

The known prostacyclin analogs are used for the treatment of pulmonal arterial hypertension (FAH) and are usually administered intravenously or in the form of an aerosol [20]; they must be administered as divided doses administered frequently throughout the day in order to meet this purpose. For the present invention, however, the prostacyclin analog is employed as target-finding structure and is not used for treating pulmonal arterial hypertension. It has been found that prostacyclin analogs in the combination according to the invention with a cationic encapsulation material and an agent have an anti-inflammatory activity and hereby further improve the activity of the conjugates according to the invention.

The second part of the conjugate according to the invention is an agent complex, i.e. an agent encapsulated by an encapsulation material. The encapsulation material serves to protect the agent and simultaneously not to interfere with, or indeed if appropriate to improve, the uptake into the cell.

The component of the conjugate according to the invention which is active as an active principle or active substance may be any agent that exerts an advantageous, healing, alleviating or modulatory activity in the cells targeted by the target-finding ligand according to the invention, with the exception of prostacyclin. Examples of agents used in accordance with the invention are, in particular, nucleic acids, peptides or polypeptides, active substances or tracers and/or derivatives of the abovementioned substances and/or mixtures of these. The agent used in accordance with the invention should preferably be an agent which is capable of alleviating or healing pulmonary conditions. In accordance with the invention, a prostacyclin analog is used in this context not as an active substance, but only as a target-finding ligand.

According to one aspect of the present invention, the agent is a nucleic acid which comprises a gene or gene fragment whose defect or deficiency brings about a pulmonary disease or which encodes an immunomodulatory-active protein, in particular an antigen. The nucleic acid may be a DNA or RNA, and it may include one or more genes or fragments. The nucleic acid may be an autonomously replicating or an integrating sequence, it may be in the form of a plasmid, a vector or another form well known to the skilled worker. It may be linear or circular and single- or double-stranded. Any nucleic acid which is active in a cell is suitable for this purpose. Moreover, the nucleic acid may include, in a manner known per se, further elements which are necessary or useful for expressing the gene for example promoters, enhancers, signal sequences and the like.

In a further embodiment, the active component of the conjugate according to the invention is a peptide, polypeptide, protein or protein fragment which is suitable for repairing a protein deficiency or a protein defect which leads to a pulmonary disease or which has an immunomodulatory activity.

Furthermore, the active component of the conjugate according to the invention can be an active substance which, when it is present in a bronchial and/or alveolar epithelial cell, leads to the healing or alleviating of a pathological state in the lungs. Examples are e.g. anti-inflammatory agents such as steroids which are employed for the treatment of asthma. Since the ligand has an anti-inflammatory action, too, this combination results in a highly effective composition.

In a further embodiment, the agent may be a reporter molecule whose uptake into the cell can provide diagnostically important information. Reporter molecules which are suitable for diagnostics are known to a person skilled in the art, and examples of suitable reporter molecules are radioactive or fluorescent tracer molecules which are known to a person skilled in the art. The reporter molecules can be employed for example for monitoring the progress of a treatment or the state of the lungs.

A further essential component of the conjugate according to the invention is an encapsulation material which encapsulates the agent to protect it from degradation or change and which does not interfere with, or indeed promotes, the introduction into the cell. The encapsulation material is suitably a cationic or neutral material, for example a polymer or any other layer-forming material. What is important is that the encapsulation material is biologically and physiologically acceptable, protects the agent during the transport, is degraded in the cell to give physiologically acceptable molecules and is inert towards the agent, i.e. does not react with the agent. Suitable encapsulation materials are known and are available in many forms. Cationic encapsulation materials are preferred for encapsulating nucleic acids, while other agents such as proteins, active substances or tracers may be encapsulated using cationic or neutral encapsulation materials.

In one embodiment of the present invention, in particular when the agent is a nucleic acid, the encapsulation material used is a cationic polymer. It has been found that cationically charged particles can be taken up by the cell more readily than neutral or anionically charged particles; however, they may also promote more unspecific attachments. Cationic encapsulation materials are preferred for encapsulating nucleic acids as the active components since nucleic acids can very readily be encapsulated, and protected, by cationic substances. Suitable methods are well known to a person skilled in the art.

The encapsulation material may be a naturally occurring, synthetic or cationically derivatized natural substance, for example a lipid or a polymer or oligomer. An example of a natural oligomer is spermine. Examples of synthetic polymers are nitrogenous biodegradable polymers, in particular those with nitrogen atoms capable of being protonated. Especially suitable are polyethyleneimines, in particular branched polyethyleneimines, which are commercially available. A suitable material is, for example, a branched polyethyleneimine with a mean molecular weight of 25 kDa, which is commercially available. It has been found that this polymer in combination with the target-finding ligands is very well tolerated. Substances which can be used as natural, optionally derivatized, layer-forming encapsulation material are also lipids, in particular cationic and neutral lipids. Lipids are available in many variants and can be used for example for forming liposomes. Especially suitable is a cationically derivatized lipid which is obtainable under the name Genzyme Lipid 67. Less suitable are polymers based on sugar molecules, such as starch or starch derivatives, and these are therefore not used as encapsulation material according to the invention.

A number of suitable polymers known to the skilled worker exist for other agents, such as proteins, active substances or tracers. Suitable are those which are biocompatible and which, at least in combination with the prostacyclin analog according to the invention, are noninflammatory or not in any other way damaging to the cell and which release the agent once it has reached the target, that is to say the cell.

The agent complex which consists of coating material and agent may consist for example of nanoparticles or nanocapsules, liposomes and the like, which are known per se and whose preparation is well known. A suitable means for example is the encapsulation in biodegradable polymers with controllable release, such as polylactide and/or polyglycolide. In this context, the coating material may be chosen such that the agent is released in a predetermined manner. Such coating materials have been described in many instances in the literature, and the skilled worker can select, from a multiplicity of materials, the material best suited to the purpose in hand.

The active agent is encapsulated with the encapsulation material, or coated therewith, in a manner known per se. This complex of agent and encapsulation material is hereinbelow also referred to as "agent complex". In the context of the present invention, "to encapsulate" means that the agent is shielded by the polymer from the physiological environment, such that it is not altered or degraded until it arrives at the target. The encapsulation may be only one layer which surrounds the agent, but it may also be a liposome or nanoparticle or microparticle in which the agent is embedded or enclosed. It may also be enclosed by complexing. A person skilled in the art is familiar with various forms of encapsulation or coating of agents, which can be employed for the conjugate according to the invention as long as they do not interfere with the binding of the target-finding ligand to the receptor and the introduction of the conjugate into the cell, and release the agent in the cell. The encapsulation of the agent with the encapsulation material, and/or the preparation of suitable particles, can be done using customary methods. In the simplest embodiment, the active agent, for example a nucleic acid, is mixed with the encapsulation material, for example a cationic polymer, such as polyethyleneimine, if appropriate in dissolved form.

At least one prostacyclin analog which is used in accordance with the invention as targeting structure is bonded to the encapsulation substance, either before the encapsulation or thereafter. Bonding the ligand to the encapsulation material does not adversely affect the activity of the agent. The bonding or immobilization of the ligand(s) must not interfere with the ability to bind to the receptor. Methods of immobilizing ligands are known to a person skilled in the art, and the known methods can be used here. A person skilled in the art can ascertain the suitability of a combination of encapsulation substance and ligand in a simple manner by preparing the desired agent complex therefrom and comparing the binding ability of the complex with the binding ability of the free ligand. Furthermore, the suitability of an encapsulation substance in respect of the agent can be ascertained by determining the activity of the agent after its release and comparing it with that of the free agent before it is encapsulated.

The ligands can be bound directly to the encapsulation material before the latter is employed for encapsulating the agent. This embodiment is preferred for example when the encapsulation material is a cationic polymer and the agent is a nucleic acid. It is also possible first to form the agent complex and thereafter to bond the ligands. This embodiment is preferred when the agent complex is made in the form of nanoparticles, nanospheres or liposomes. If appropriate, the bonding of the ligand to the encapsulation material may also be effected via a spacer so that the site of the ligand which has binding activity is available for the binding. This gives rise to a conjugate in which the active agent is not influenced by the bond and in which the at least one prostacyclin analog on the surface is freely available for binding to the $IP_1$ receptor. The ligand, i.e. the prostacyclin analog, can be bonded to the encapsulation material by any type of bond such as covalent bond, ionic bond or coordinative bond, hydrogen bond formation and the like, as long as the bond suffices to immobilize the ligand and as long as its ability to bind to the receptor is not adversely affected. Thus, the prostacyclin analog may be coupled to the encapsulation material for example via a covalent or ionic bond, directly or via a spacer. An example of a spacer which is known to a person skilled in the art is polyethylene glycol (PEG).

The degree of coupling, i.e. the extent to which the conjugate, or the encapsulated particles, is/are loaded with ligands, expressed as ligand per conjugate particle, affects the release of the agent and therefore the activity of the agent in the cell. The amount of ligands to be bonded to an encapsulated particle should preferably not be unduly high since otherwise the targeting of the receptor might be interfered with as a result of steric hindering. A person skilled in the art can find out the ideal degree of loading by routine experiments. The amount of ligands depends on the nature of the encapsulation material and the size of the particles.

It has also been found that a high degree of coupling can lead to the release of the agent only being incomplete. If a cationic polymer is used for the encapsulation, the degree of coupling should therefore amount to 15 ligands per polymer or less. On the other hand, at least one prostacyclin analog must be bonded to each encapsulated particle in order to bring about the targeting.

In each case one type of prostacyclin analog may be bonded per conjugate or particle. It is also possible to bind a mixture of two or more prostacyclin analogs so as to enhance the binding ability and/or the uptake into the cell, if appropriate.

It has been found that the ratio of encapsulation material to active agent may affect the activity. If not enough encapsulation material is present, the active agent is not protected sufficiently. If the proportion of the encapsulation material is too high, then firstly compatibility problems may result and secondly an unduly high proportion of encapsulation material may lead to the release of the active agent becoming impossible. In both cases, the efficiency of the transfer suffers. A person skilled in the art can find out the ratio which is best suitable in each case in few routine experiments. A ratio of encapsulation material to active agent in the range of from 10:1 to 1:4, based on weight, has proved to be particularly suitable. A ratio of encapsulation material to agent of from 4:1 to 1:4 is especially preferred. If the conjugate comprises a nucleic acid as the agent and polyethyleneimine as the polymer, the proportion of the polymer may also be indicated by the molar ratio of polymer nitrogen content to DNA phosphate content; this ratio is preferably in the range of from 2 to 10, especially preferably from 4 to 8. It has been found that the hydrodynamic diameter of the conjugate particles in a molar ratio of polymer nitrogen content to DNA phosphate content of 4 to 8 is in the range of from 50 to 100 nm, which is the optimum for the uptake characteristics.

Furthermore, it has been found that optimal conjugates are obtained when the ligand loading density is adapted to the degree of encapsulation. If the proportion of encapsulation material is relatively high, the loading density should not be too great since the agent is otherwise shielded unduly. If the proportion of encapsulation material is in the lower range, the loading density may, correspondingly, be in the upper range.

It has been found that the conjugate according to the invention is an ideal agent for introducing active substances into bronchial and/or alveolar epithelial cells. While only 5% or less of the particles without target ligands or targeting ligands which are described in the prior art reach their target, viz. the cell, and while also only 50% or less of the ligand-containing conjugates described in the prior art reach the target and can exhibit their function, it has been demonstrated experimentally for the conjugates according to the invention that more than 50%, frequently 60% and more, indeed up to 80%, of the conjugate according to the invention are taken up by cells and release their agent.

Thus, a means is provided via which an active component is introduced into target cells in a highly efficient manner, where on the one hand the active agent is well protected during the transport into the cell so that the proportion of active agent which reaches the cell is very high, and, secondly, the uptake efficiency is very high owing to the structure of the conjugate according to the invention.

In a further embodiment the conjugate according to the invention can be improved still further by additionally providing the particle encapsulated with encapsulation material, for example a cationic polymer, with polyethylene glycol chains so as to further increase the survival time in the lungs. Protecting active molecules such as nucleic acid by PEGylation is known per se, and the usual methods may be used here.

The conjugate according to the invention can be used for treating various pulmonary diseases. In particular, the conjugate according to the invention is suitable for curing or alleviating pulmonary diseases due to gene or protein defects. An example thereof is cystic fibrosis. As mentioned hereinabove, it is possible not only to introduce the lacking or deficient gene into the cell, but also to introduce into the cell a protein encoded by the lacking or deficient gene.

A further field of application for the conjugates according to the invention is the use as vaccine. In this embodiment, the active component of the conjugate is either an immunomodulatory or immunologically active peptide or protein or a gene which encodes an immunomodulatory or immunologically active protein or peptide [1,2]. An advantage of this embodiment of the invention is that a vaccine can be administered via the lungs in a noninvasive manner, for example using a nebulizer or an aerosol. This technology is uncomplicated, makes possible the use even in locations where the administration of injections is problematic due to the hygienic circumstances or due to the lack of a suitably trained workforce, and makes possible an uncomplicated multiple dosage so as to enhance the immune response. Moreover, the lungs, due to their large surface area and the presence of immunologically active cells, are well suited to vaccination purposes.

The conjugate according to the invention is provided for administration into the lungs. To this end, it may be formulated in a manner known per se as a pharmaceutical composition which is introduced into the lungs via inhalation or via nebulization. Suitable formulations are known to a person skilled in the art. Thus, the conjugate may be prepared as a suspension or emulsion via a nebulizer or as an aerosol, with an inert gas as the carrier. It may also be employed as a powder.

The present invention is illustrated in greater detail by the examples which follow without being limited to this example.

EXAMPLE 1

Conjugates of particles coated with an encapsulation material and with iloprost or treprostinil as target-finding structure are prepared and studied.

Materials and Methods

The suppliers of chemicals and plasmids and the concentrations used are as follows:

Iloprost, treprostinil and CRY 10449: Cayman Chemicals (Michigan, USA)

Branched polyethyleneimine (average molecular weight 25 kDa), N-hydroxysulfosuccinimide (sulfo-NHS), bovine serum albumin (BSA), sodium phosphate, picrylsulfonic acid solution, 4-(2-hydroxyethyl)piperazine-1-ethanesulfonic acid (HEPES) and heparan sulfate: Sigma Aldrich (Schnelldorf, Germany)

PEI was diluted in double-distilled water (water for injection, B. Braun Melsungen AG, Melsungen, Germany), and the pH was brought to 7 using aqueous hydrochloric acid.

Sodium phosphate was dissolved in double-distilled water to a concentration of 0.5 mM and the pH was brought to 7.5 using sodium hydroxide.

HEPES was dissolved in distilled water to a concentration of 0.1 M, and the pH was brought to 7.4 using sodium hydroxide.

Heparan sulfate was dissolved in double-distilled water to a concentration of 5 mg/ml.

Ethanol (analytical grade) and 3-(N-morpholino)propanesulfonic acid (MOPS): Merck (Darmstadt, Germany)

MOPS was dissolved in double-distilled water to a concentration of 0.1 M, and the pH was brought to 6 using aqueous hydrochloric acid.

1-Ethyl-3-(3-dimethylaminopropyl)carbodiimide hydrochloride (EDC) and 5-(and 6-)carboxyfluorescein succinimidyl ester (Fluorescein-NHS): Pierce (Rockfort, USA)

Dithiothreitol (DTT): Amersham Biosciences (South San Francisco, USA)

D-Luciferin: Synchem OHG (Flensberg/Altenburg, Germany)

The plasmids pCMV-luc, which contained the *Fotinus pyralis* luciferase gene under the control of the early cytomegalovirus (CMV) promoter, and pCpG-luc were propagated in *E. coli* and provided in highly purified form (LPS content≤0.1 E.U./μg DNA) by Plasmid Factory GmbH (Bielefeld, Germany). The amount of Supercoil pDNA was ≥90% ccc (covalently closed circular) for pCMV-luc and ≥98% ccc for pCpG-luc.

Cell Lines Employed

A549 cells (human alveolar epithelial cells): DSMZ (deutsche Sammlung für Mikroorganismen und Zellkulturen [German Collection of Microorganisms and Cell Cultures], Braunschweig, Germany)

BEAS-2B (human bronchial epithelial cells), H441 (human bronchiolar epithelial cells): ATCC (American Type Culture Collection)

16HBE14o-cells: human bronchial epithelial cells

A549, BEAS-2B and 16HBE14o-cell lines were grown at 37° C. in a humidified atmosphere of 5% $CO_2$ in air in minimal essential medium (MEM, Gibco-BRL, Karlsruhe, Germany), supplemented with 10% fetal calf serum (FCS, Gibco-BRL, Karlsruhe, Germany). The H441 cell line was grown at 37° C. in a humidified atmosphere of 5% $CO_2$ in air in Roswell Park Memorial Institute medium 1640 (RPMI1640, Gibco-BRL, Karlsruhe, Germany), supplemented with 10% FCS.

Animals 14-week-old female BALB/c mice (Charles River Laboratories Sulzfeld, Germany) were kept under specific pathogen-free conditions. Before the experiments, the mice were acclimatized for at least 7 days. All animal procedures were approved and were checked by the local ethics commission and carried out following the guidelines of the German Recht zum Schutz von Tierleben [German Law on the Protection of Animal Life].

Western-Blot Analysis

A549-, BEAS-2B and 16HBE14o-cells were washed with PBS and lysed on ice in lysis buffer comprising 20 mM Tris-HCl (pH 7.5), 100 mM NaCl, 1 mM EDTA, 1% Triton X-100 and 0.05% sodium deoxycholate. 1 mM DTT and protease inhibitor cocktail (Roche Diagnostics GmbH, Mannheim, Germany) were added freshly directly before use. The protein concentrations were determined using a Biorad protein assay (Biorad, Munich, Germany). For each cell line, 50 μg of protein were diluted in SDS sample loading buffer (62.5 mM Tris-HCl (pH 6.8), 2% SDS, 10% glycerol, 2% DTT, 0.001% bromophenol blue), which had been boiled for 5 min, separated on a 7.5% Tris-HCl gel (Biorad, Munich, Germany) and transferred on to a PVDF membrane (Millipore, Schwalbach, Germany). The membranes were blocked at room temperature for 1 h with TBS-T (20 mM Tris-HCl (pH 7.6), 137 mM NaCl, 0.1% Tween-20) which comprised 5% skim milk powder (Sigma Aldrich, Deisenhofen, Germany). The primary polyclonal antibody (dilution 1:500) for the $IP_1$ receptor (Cayman Chemical, Michigan, USA) was incubated overnight in 0.5% skim milk. The membranes were washed with TBS-T and incubated with a secondary HRP-conjugated anti-rabbit antibody (dilution 1:15 000; Biorad, Munich, Germany) for 1.5 h at room temperature in 0.5% skim milk. After several wash steps with TBS-T, detection was carried out by chemiluminescence using an ECL Detection Kit (Pierce, Rockfort, USA) following the manufacturer's instructions.

Synthesis of Fluorescein-BSA-Iloprost (FLUO-BSA-ILO) and Fluorescein-BSA-Treprostinil (FLUO-BSA-TRP)

20 mg (0.3 μmol) of BSA were diluted in 2.5 ml of sodium phosphate buffer, pH 7.5, and mixed with a ten-fold molar excess of fluorescein-NHS. After stirring for one hour at room temperature, the mixture was purified on a PBS-equilibrated Sephadex G25 MPD-10 column (GE Health Care, Uppsala, Sweden). Either 0.7 mg (1.8 μmol) of ILO or 0.8 mg (1.8 μmol) of TRP were dissolved in 130 μl of analytical-grade ethanol and mixed with 370 μl of MOPS buffer, 0.1 M, pH 6. 0.5 mg (5 mM) of sulfo-NHS (in MOPS buffer) and 0.2 mg (2 mM) of EDC (in MOPS buffer) were added and the mixture was stirred for 15 min at room temperature. Thereafter, 5 μl (20 mM) of DTT (in distilled water) were added, and 3 mg (45.2 nmol) of FLUO-BSA in 190 μl and 210 μl of phosphate buffer 0.5 M were immediately pipetted into the reaction mixture. After the mixture had been stirred for two hours at room temperature, it was purified on a PBS-equilibrated Sephadex G25 MPD-10 column (GE Health Care, Uppsala, Sweden). The amounts of BSA were evaluated quantitatively in a Biorad protein assay using a BSA standard curve. The coupling efficiency of the final products and intermediates were determined by TNBS assay [21], and the absorption was measured at 495 nm. The degree of coupling of BSA-ILO and BSA-TRP was found to be 10 mol ILO or TRP per mol BSA.

Synthesis of Iloprost-Grafted PEI Polymers (PEI-g-ILO)

Various degrees of coupling of PEI-g-ILO were synthesized by varying the amounts of EDC which were added to the reaction mixture. 1 mg (2.8 μmol) of ILO was diluted in 100 μl of analytical-grade ethanol, and mixed with 68 nmol of PEI in 900 ml of HEPES buffer, 0.1 M, pH 7.4, and 1 mg (5 mM) of sulfo-NHS. Various amounts of EDC were added to a final concentration of 25 mM, 50 mM, 60 mM or 100 mM, respectively, and the mixtures were incubated at room temperature for 4 h, with stirring. The reaction mixture was purified on a Sephadex G25 MPD-10 column (GE Health Care, Uppsala, Sweden) which had been equilibrated with double-distilled water. The PEI concentration was determined in a $CuSO_4$ test as described by Ungaro et al. [22]. $^1$H-1D NMR spectra of PEI-g-ILO were recorded in $D_2O$ in a Bruker AV 250 MHz spectrometer. The degrees of coupling of PEI-g-ILO were calculated by integrating the broad multiplet of PEI ($CH_2$—$CH_2$—NH—) at δ (1H)=2.5 to 3.1 ppm and the singlet of the terminal methyl group of ILO (—C≡C—$CH_3$) at δ (1H)= 1.73 ppm. The covalent conjugation of ILO to PEI resulted in four different degrees of coupling ($F_{ILO}$(mol ILO/mol PEI)=

2, 5, 8, 16). PEI-g-ILO constructs were divided into small aliquots, shock-frozen in liquid nitrogen and maintained at −80° C. until further use.

Incubation Experiment with FLUO-BSA-ILO and FLUO-BSA-TRP

The receptor binding/uptake of FLUO-BSA-ILO was studied in A549, H441, 16HBE14o- and BEAS-2B cells. For the FACS measurement experiments, 100 000 cells/well were seeded in 24-well plates (TPP, Trasadingen, Switzerland) 24 hours before adding the conjugates. FLUO-BSA-ILO, FLUO-BSA-TRP and FLUO-BSA conjugates were diluted in MEM to a concentration of 0.5 µM, and the cells were incubated at 37° C. for 4 h. After the cells had been washed with PBS, the cells were removed from the wells by treatment with trypsin, and the FACS measurements were carried out using a Beckton-Dickinson FACS scan (San Jose, USA). For the confocal laser scanning microscopy, the experiments were carried out on slides with 4 chambers from BD Falcon Culture (BD Biosciences San Jose, USA) with 25 000 cells per chamber. The incubation of FLUO-BSA-ILO and FLUO-BSA was performed as described above. The cells were washed and fixed in 4% paraformaldehyde, and the nuclei were subsequently stained with 0.33 µM DAPI (4',6-diamidino-2-phenylindole) and F-actin with Alexafluor® 568 Falloidin (Invitrogen GmbH, Karlsruhe, Germany) using standard protocols. The slides were covered with medium (Vectashield, Vector Laboratories Inc., Berlingame, USA), and images were taken with a confocal laser scanning microscope (Leica, Solms, Germany).

Experiment on the Inhibition of the Binding of FLUO-BSA-ILO to CAY10449

The inhibition of the receptor binding/uptake of FLUO-BSA-ILO was studied on 16HBE14o-cells. 24-well plates were prepared as described above. CAY10449 was diluted in MEM to concentrations of 15 µM, 30 µM and 150 µM, and the mixtures were incubated at 37° C. for 15 min. Immediately thereafter, FLUO-BSA-ILO and FLUO-BSA were added to a final concentration of 25 nM and incubated together with the cells at 37° C. for 4 h. The binding/uptake was measured using FACS.

Preparation of the Gene Vector Particles

Plasmid comprising luciferase reporter gene (pCMV-luc), and PEI or PEI-g-ILO were diluted separately in 25 µl of double-distilled water. Various N/P ratios (molar ratio of PEI nitrogen to DNA phosphate) were tested. The pCMV-luc solution was added to an identical volume of the polymer solution and mixed carefully by pipetting up and down eight times, which resulted in particles with a concentration of 20 µg pCMV-luc/ml. The gene transfer particles were incubated at room temperature for 20 min.

Measuring the Particle Size

The particle size (determined by dynamic light scattering) was measured using a Zeta PALS/Zeta Potential Analyzers (Brookhaven Instruments Corporation, Vienna, Austria). Gene vector particles were generated as described hereinabove. The following settings were used: 5 runs with 1 min of measurement per sample; viscosity for water 0.89 cP; ref. Index 1.330; temperature 25° C.

DNA Retardation Assay

PEI/pCMV-luc and PEI/g-ILO/pCMV-luc gene vector particles with various degrees of coupling with N/P=4 were prepared in double-distilled water as described above. 5 µl of each particle solution was mixed either with 2 µl of double-distilled water or 2 µl of heparan sulfate solution (5 mg/ml). After incubation for 45 minutes, samples were mixed with 1 µl of loading buffer (0.25% bromophenol blue, 0.25% xylene cyanol FF, 30% glycerol in water), loaded into individual wells of a 0.8% agarose gel and separated by agarose gel electrophoresis for 1 h at 125 V. The gel was stained with ethidium bromide and the DNA bands were visualized under UV light.

In-Vitro Transfection Studies 24 h before the transfection, A549, 16HBE14o- and BEAS-2B cells were seeded into 24-well plates (TPP, Trasadingen, Switzerland) at a density of 100 000 cells/well and grown in MEM containing 10% of FCS supplemented with 0.1% (v/v) penicillin/streptomycin. Before the transfection, the cells were washed with PBS, and 450 µl of fresh serum-free medium were added per well. Thereafter, 50 µl of the gene vector particles, corresponding to 1 µg of pCMV-luc, were pipetted on to the cells. For the inhibition experiments, CAY10449 was added to fresh medium at a concentration of 150 µM 15 min before adding the gene vector particles. After incubation for 4 hours, the transfection medium was replaced by MEM which comprises 10% of FCS and had been supplemented with 0.1% (v/v) penicillin/streptomycin. 24 h after the transfection, the luciferase activity was measured using a Wallac Victor$^2$ 1420 multilabel counter (Perkin Elmer, Boston, USA) as described by Huth et al. [23]. The results were normalized to total cell protein content using a Biorad protein assay and BSA as the protein standard.

In-Vivo Gene Transfer Studies

To prepare gene vector particles for the aerosol delivery to mice, pCpG-luc and PEI or PEI-g-ILO $F_{ILO}$=5 were diluted in each case with 4.0 ml of water for injection (B. Braun Melsungen AG, Melsungen, Germany), which resulted in concentrations of 250 µg/ml of pCpG-luc and 130.4 µg/ml PEI, respectively (corresponding to an NAP ratio of 4). The pCpG-luc solution was pipetted to the PEI solution, mixed by pipetting up and down 8 times, which resulted in a final DNA concentration of 125 µg/ml. The particles were incubated at room temperature for 20 min before use. The particles were nebulized using a PARI Turboboy® N inhalation device with a PARI LC+ nebulizer (PART GmbH, Starnberg, Germany) which had been connected to a vertical whole-body aerosol device as described by Rudolph et al. [24]. After 24 h, mice were anesthetized and a pulmonal administration of D-luciferin substrate (1.5 mg/50 µl PBS per mouse) was given by sniffing [25]. After 10 min, the bioluminescence was measured (IVIS 100 Imaging System; Xenogen, Alameda, USA) using the following camera settings: field of vision 10, F1 f-stop, high resolution binning and exposure time 10 min. To confirm the degrees of expression of the reporter gene in the lungs, the mice were sacrificed by cervical dislocation after the in-vivo bioluminescence imaging. After opening the peritoneum by section along the midline, the lungs of the animals were dissected and perfuzed with PBS. The lungs were shock-frozen in liquid nitrogen and homogenized in the frozen state. After the addition of 400 µl of lysis buffer (250 mM Tris, pH 7.8, 0.1% Triton X-100, Roche Complete Protease Inhibitor Cocktail Tablets) and incubation on ice for 20 minutes, the luciferase activity in the supernatant was measured using a Lumat LB9507 tube luminometer (EG & G Berthold, Munich, Germany). Recombinant luciferase (Roche Diagnostics GmbH, Mannheim, Germany) was used as the standard for calculating the amount of luciferase which was expressed in the pulmonary tissue.

MTT-Based Assay

The toxicity of PEI/pCMV-luc or PEI-g-ILO $F_{ILO}$=5/pCMV-luc particles was evaluated on 16HBE14o-cells with an N/P ratio of 4. 24 h before the experiment, the cells were seeded into a 24-well plate at a density of 80 000 cells/well. The transfection was performed as described above. After 4 h, the transfection mixture was replaced by 400 µl of medium, and an MTT-based test was carried out using the Cell Proliferation Kit 1 (Roche Diagnostics GmbH, Mannheim, Germany) following the manufacturer's instructions. Untreated cells were used as reference by setting the corresponding absorption as 100% viable cells.

Collecting Serum and Analyzing the Cytokine Concentration 24 h after the delivery of the aerosol, blood samples were taken from the mice and stored at 4° C. overnight. The blood was centrifuged and the serum was collected. Interleukin-12 (IL-12) and interferon-γ (IFN-γ) were determined quantitatively using the mouse IL-12 (P40/P70) and the mouse INF-γ-ELISA kits (Ray Biotech, Norcross, USA) following the manufacturer's instructions. Untreated mice were used as reference by setting the corresponding concentration as 1.

Statistic Analysis

The results are shown as mean±standard deviation. Statistically significant differences were evaluated by the unpaired Student's T-test. p<0.01 was considered to be significant.

Results

Confirmation of the $IP_1$ Receptor Expression in Pulmonary Cells by Western Blot The expression of $IP_1$ receptor in human alveolar (A549) and bronchial (BEAS-2B, 16HBE14o-) epithelial cells was confirmed by Western blot analysis. A protein band at 47 kDa was detected (FIG. 1), which corresponds to the glycosylated form of the $IP_1$ receptor protein expressed on the cell membrane [26]. It was therefore investigated whether the targeted addressing of the $IP_1$ receptor for the delivery of proteins or genes is possible.

Addressing Pulmonary Cells with Different $IP_1$ Receptor Ligands

Figure 2:
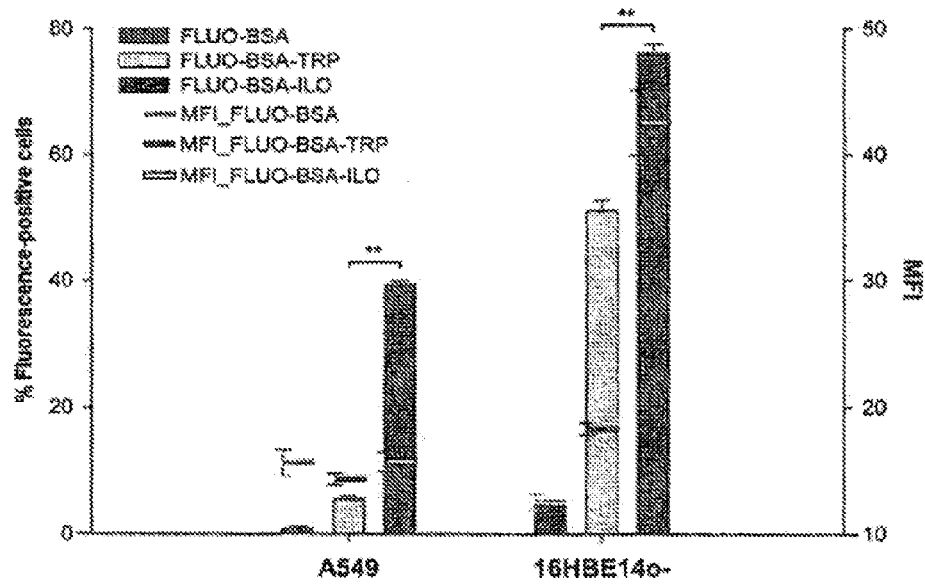

To study the targeting toward the $IP_1$ receptor for the receptor-mediated gene transfer, TRP and ILO were coupled chemically to fluorescein-labeled bovine serum albumin (FLUO-BSA), which acted as model substance. While the incubation of A549 and 16HBE14o-cells with FLUO-BSA resulted in unspecific background binding, the incubation with FLUO-BSA-TRP and FLUO-BSA-ILO resulted in 5.5±0.5% and 39.3±0.6% positive A549 cells and 51±1.8% and 76.1±1.4% positive 16HBE14o-cells, respectively (FIG. 2). The mean fluorescence intensity (MFI) of A549 and 16HBE14o-cells was significantly higher following incubation with FLUO-BSA-ILO than after incubation with FLUO-BSA-TRP. These results demonstrate that TRP and ILO are capable of mediating successful binding of the model substance FLUO-BSA to pulmonary cells, but that ILO is the more effective targeting ligand.

Specificity of the FLUO-BSA-ILO Binding to Various Pulmonary Cell Lines

Figures 3A, 3B:
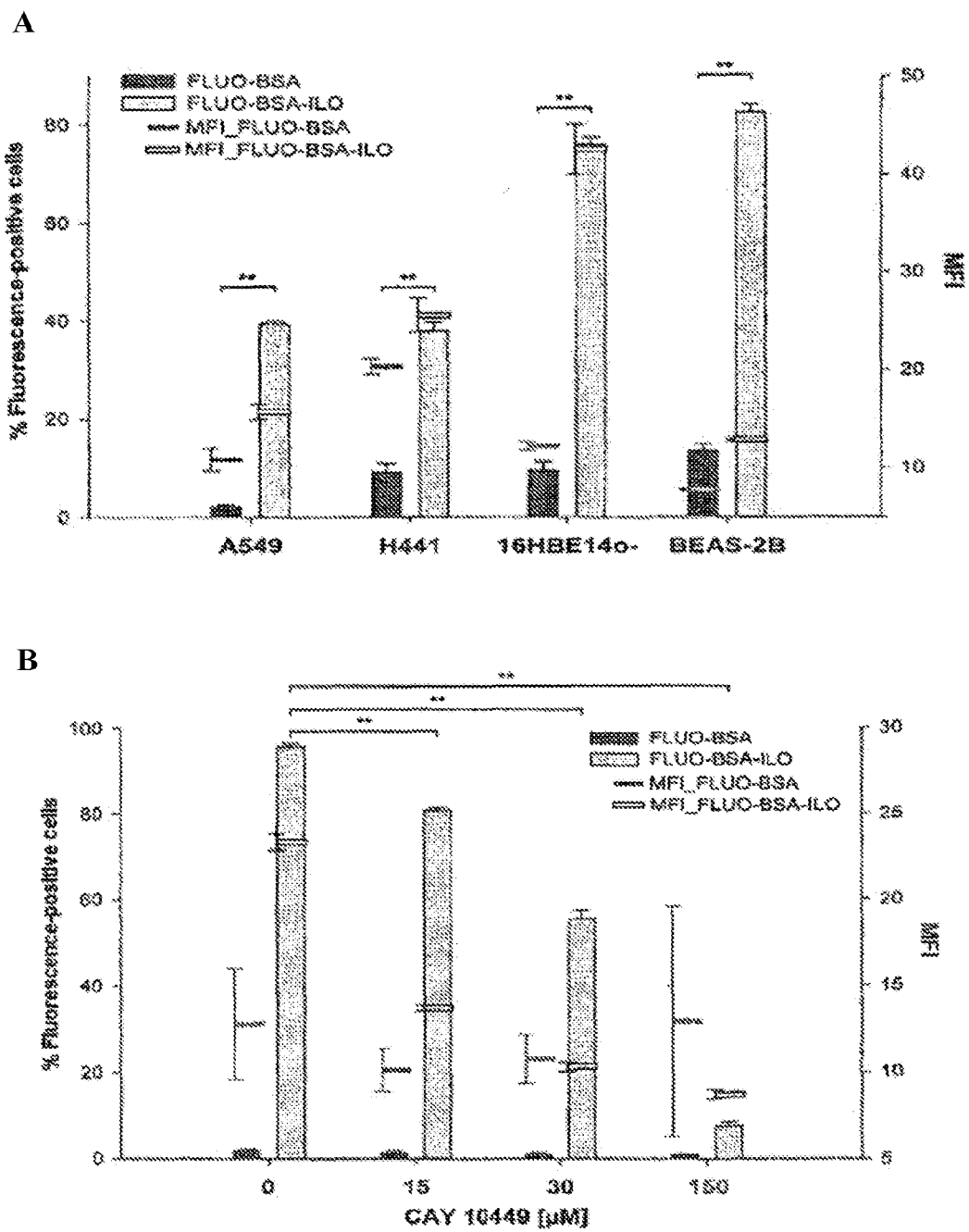

ILO was further investigated as targeting ligand on additional pulmonary cell lines owing to the better cell binding/uptake in comparison with TRP. In addition to A549 and 16HBE14o-cells, the incubation of H441 and BEAS-2B cells with FLUO-BSA-ILO generated a significantly higher number (p<0.01) of positive cells and MFI than the control FLUO-BSA (38.0±1.8%) and 82.7±1.6%, respectively, in comparison with 9.1±1.9% and 13.7±1.2%, respectively (FIG. 3A). This effect was more pronounced on human bronchial epithelial cells (16HBE14o-, BEAS-2B) than in clara (H441) or alveolar (A549) epithelial cells. These results demonstrate the different cell surface expression of $IP_1$ receptor in types of human pulmonary cells.

To confirm the receptor specificity of the observed binding of FLUO-BSA-ILO in pulmonary cells, 16HBE14o-cells were incubated with FLUO-BSA-ILO in the presence of increasing amounts of CAY10449. This compound has already been reported earlier as being a highly-specific potent antagonist of the human $IP_1$ receptor [27, 28]. 16HBE14o-cells were incubated with 25 nM of FLUO-BSA-ILO together with increasing concentrations of CAY10449. The addition of CAY10449 resulted in a significant dose-dependent reduction (p<0.01) of not only the number of fluorescence-positive cells, but also of the MFI (FIG. 3B). At the highest CAY10449 concentration used, the number of fluorescence-positive cells dropped from 95.7±0.7% to 7.4±0.9%. The cells which had been incubated with FLUO-BSA conjugates were used as controls and showed no activity upon the addition of CAY10449. Similar results were obtained in competitive experiments with an excess of unconjugated ILO.

Figure 3C:
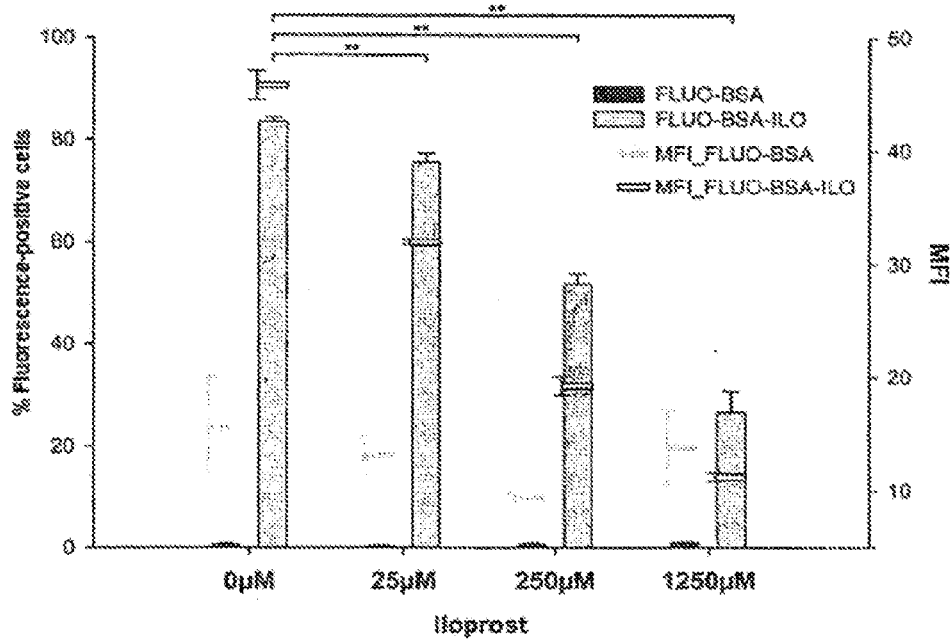
Figure 3D:
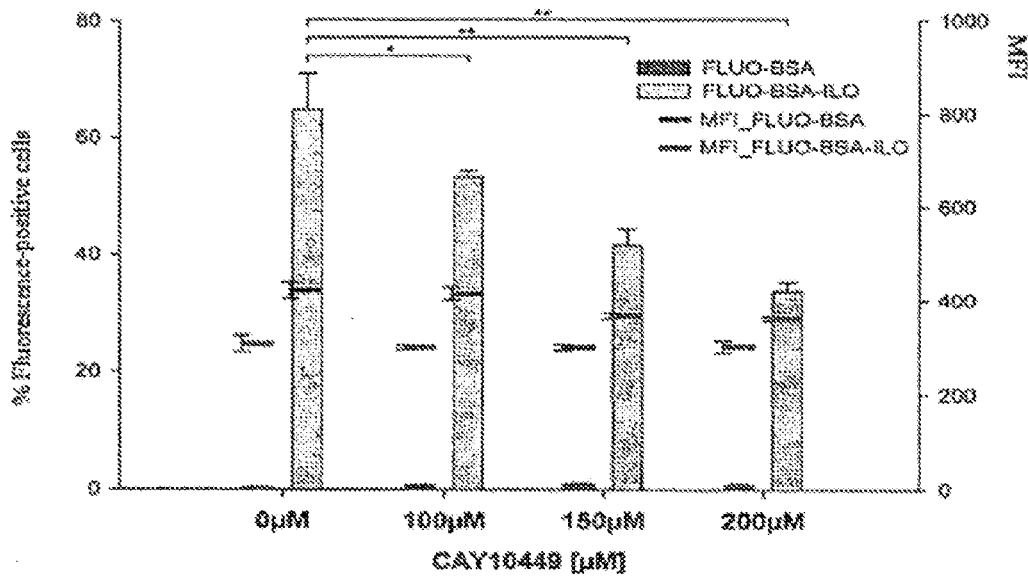
Figure 3E:
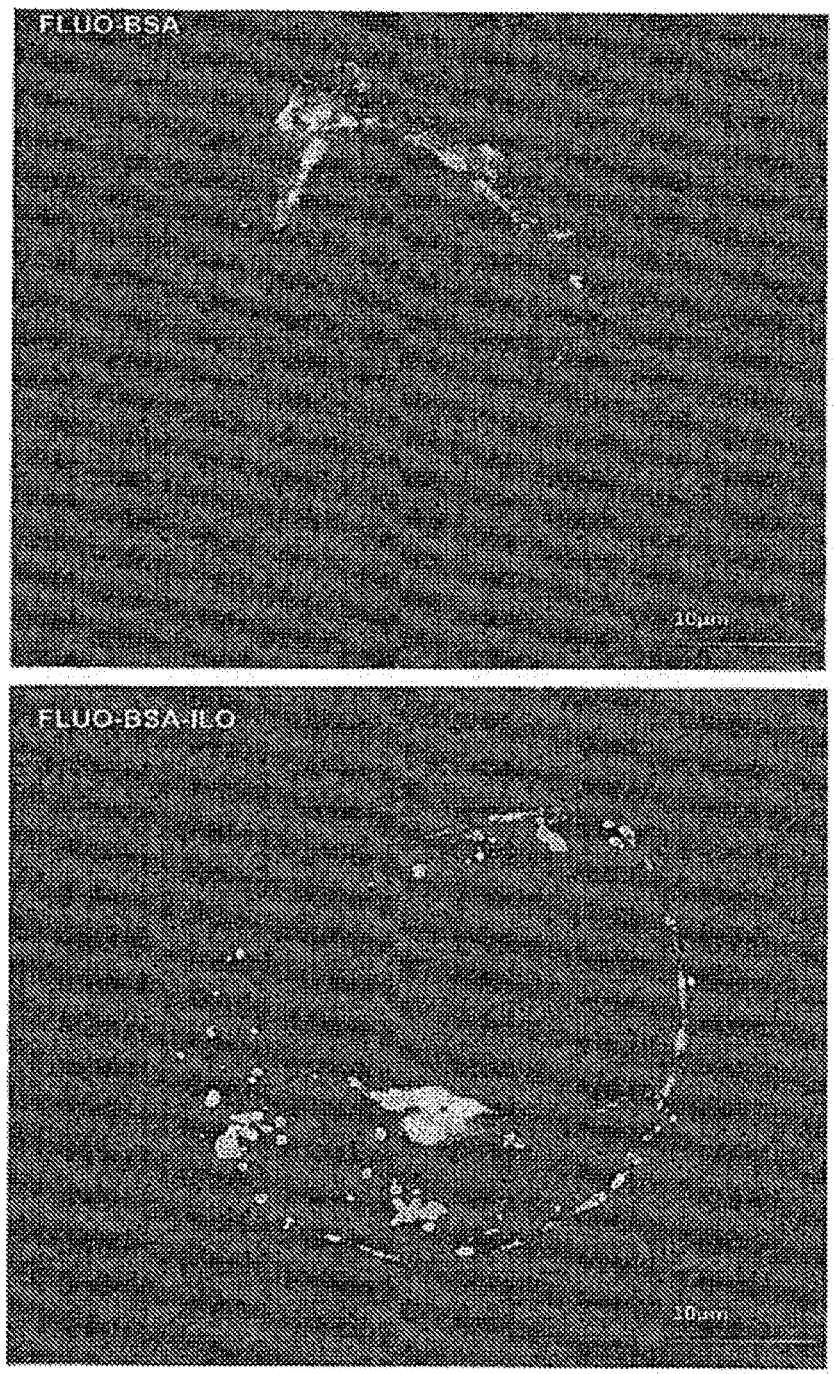
Figure 4:
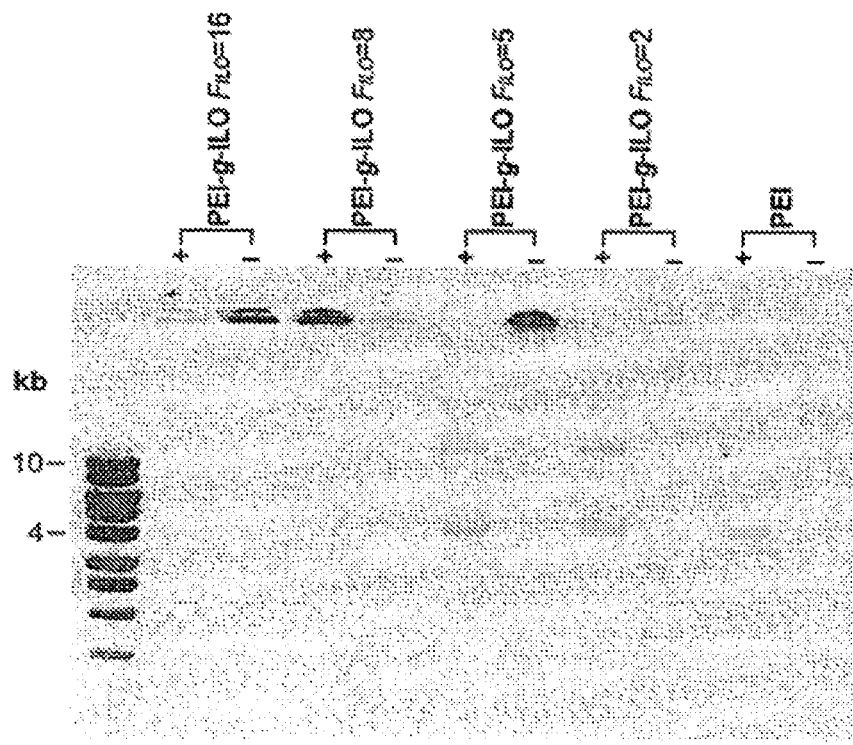

FACS measurements together with inhibition experiments suggest a cell-type-dependent cell surface expression of $IP_1$ receptor on pulmonary epithelial cells. To test further whether ILO mediates the intracellular uptake of FLUO-BSA-ILO, additional experiments were carried out using confocal laser scanning microscopy. 16HBE14o-cells were incubated either together with 0.5 μM FLUO-BSA or FLUO-BSA-ILO. The visualization of the cells by confocal microscopy demonstrated a clear cell surface binding followed by the intracellular uptake of FLUO-BSA-ILO conjugates (FIG. 3C), whereas no uptake of FLUO-BSA was observed.

Characterization of PEI and PEI-g-ILO Gene Vector Particles

Figure 5A:
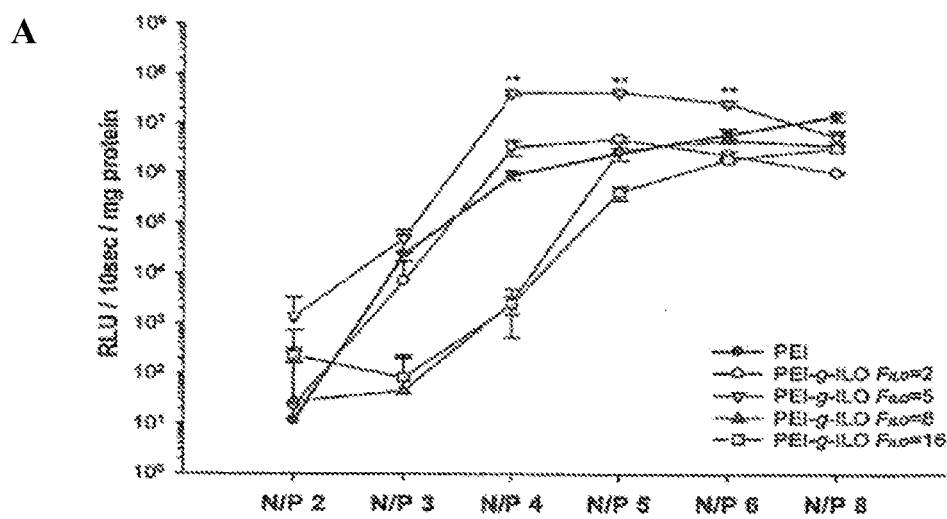
Figure 5B:
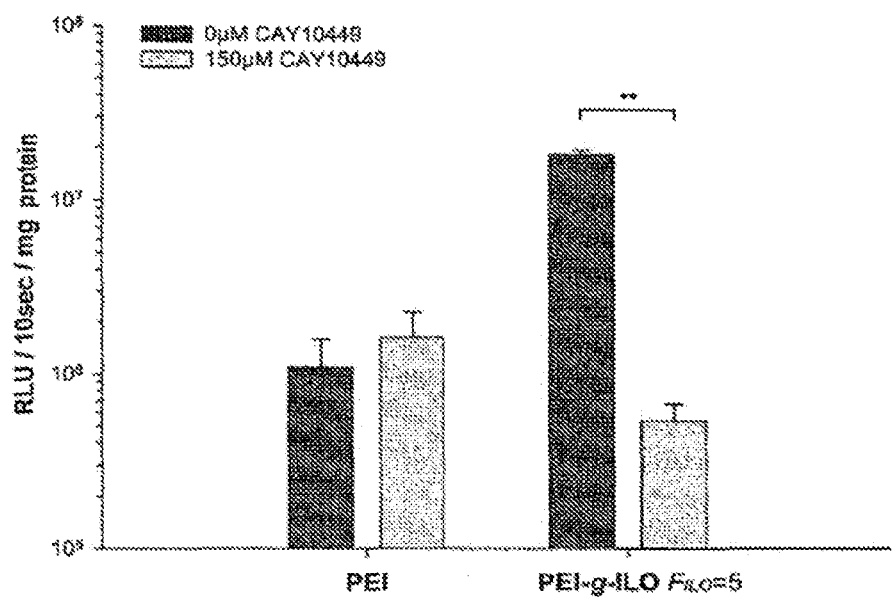

ILO was coupled to PEI via carbodiimide chemistry $F_{ILO}$=2, 5, 8 and 16, and the size of the resulting gene vector particles was measured by dynamic light scattering (Table 1). Particles with a degree of coupling $F_{ILO}$=2 and 5 with an N/P ratio of from 4 to 8 had hydrodynamic diameters of from 50 to 100 nm, which was comparable to PEI gene vectors. Particles which have been prepared with PEI N/P 2, PEI-g-ILO $F_{ILO}$=2 N/P 2 to 3 and PEI-g-ILO $F_{ILO}$=16 N/P 4 were unstable and precipitated. Particles smaller than 150 nm had a polydispersity of <0.2.

The next step was to determine the DNA binding affinity of the PEI-g-ILO constructs. Particles with N/P 4 were prepared, and a DNA release assay was carried out (FIG. 4). For PEI, PEI-g-ILO $F_{ILO}$=2 and PEI-g-ILO $F_{ILO}$=5, the addition of heparan sulfate resulted in complete release of the DNA. For a high degree of coupling of 16, only a partial release of the DNA was observed, which suggests a stronger binding of the polymers to the plasmid. A degree of coupling of 16 or more is therefore less preferred.

In-Vitro Transfection Efficiency

An increased binding and uptake of FLUO-BSA-ILO in various pulmonary cells and the possibility of forming PEI-g-ILO/pCMV-luc particles was the reason for studying ILO as ligands further in order to improve the gene transfer in-vitro. 16HBE14o-cells were transfected with PEI-g-ILO gene vectors and compared with unmodified PEI as the control. The gene transfer efficiency increased with the N/P ratio. The highest degree of gene expression was found for N/P 4 and $F_{ILO}$=5. Under these optimized conditions, the gene expression was significantly 46 times higher than for PEI (FIG. 5A). The particle formation with higher N/P ratios (>4) did not result in any further increase in gene expression. PEI-g-ILO conjugates with other degrees of coupling resulted either in lower or equal transfection grades in comparison with PEI.

The experiments on the competitive inhibition with CAY10449 were carried out to confirm the receptor-mediated gene transfer of PEI-g-ILO gene vectors. 16HBE14o-cells were transfected either with PEI or PEI-g-ILO $F_{ILO}$=5 gene vectors with N/P 4 in the presence or absence of 150 μM CAY10449. The gene expression observed for PEI-g-ILO $F_{ILO}$=5 was significantly ($p<0.01$) 33 times reduced over PEI (FIG. 5B). No effect by CAY10449 was observed in cells which have been transfected with PEI.

Figure 5C:
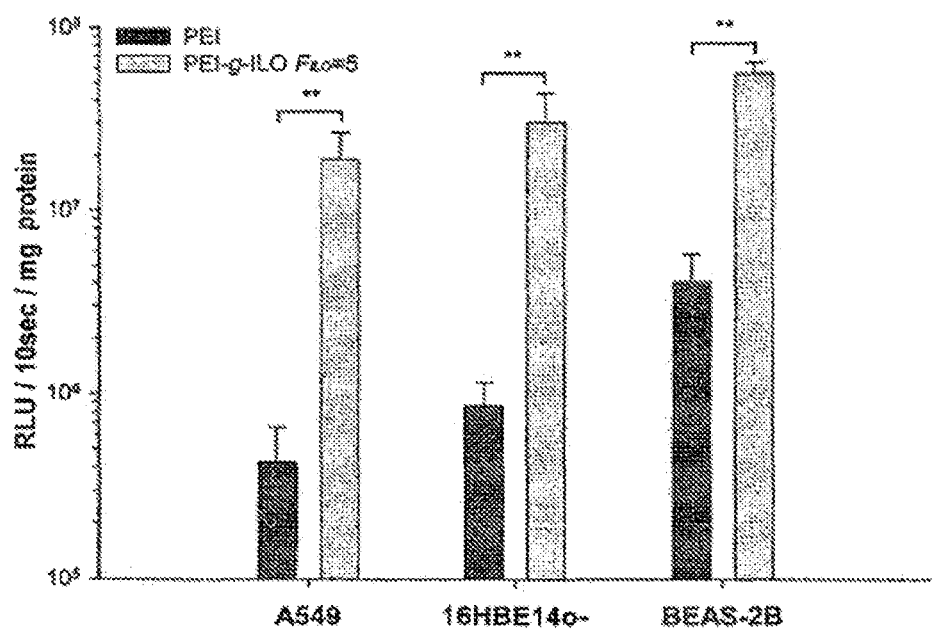

Furthermore, PEI-g-ILO $F_{ILO}$=5 was also tested on A549 and BEAS-2B cells. Under optimized conditions, the expression mediated by PEI-g-ILO $F_{ILO}$=5 was 45 times and 14 times higher than PEI in A549 and BEAS-2B cells, respectively (FIG. 5C).

Investigations into the Gene Release In-Vivo

Figure 6A:
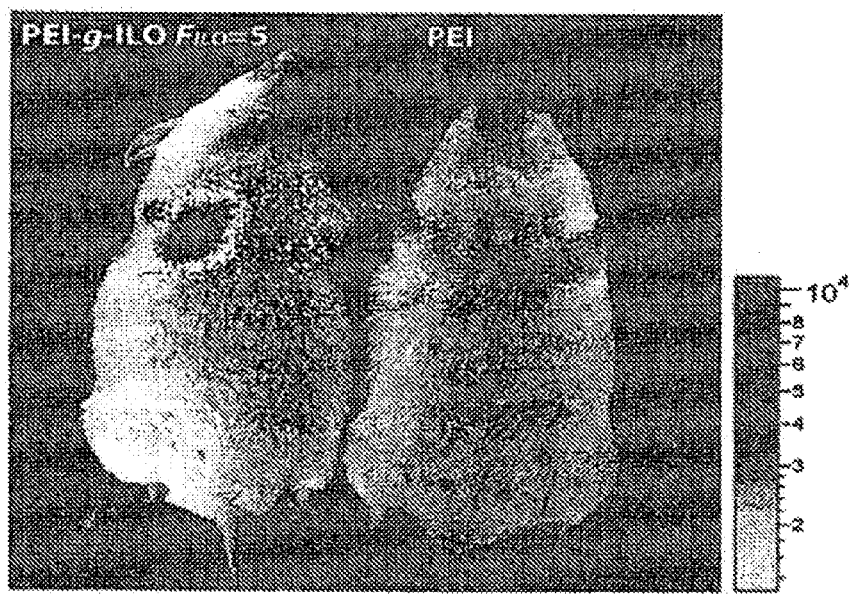
Figure 6B:
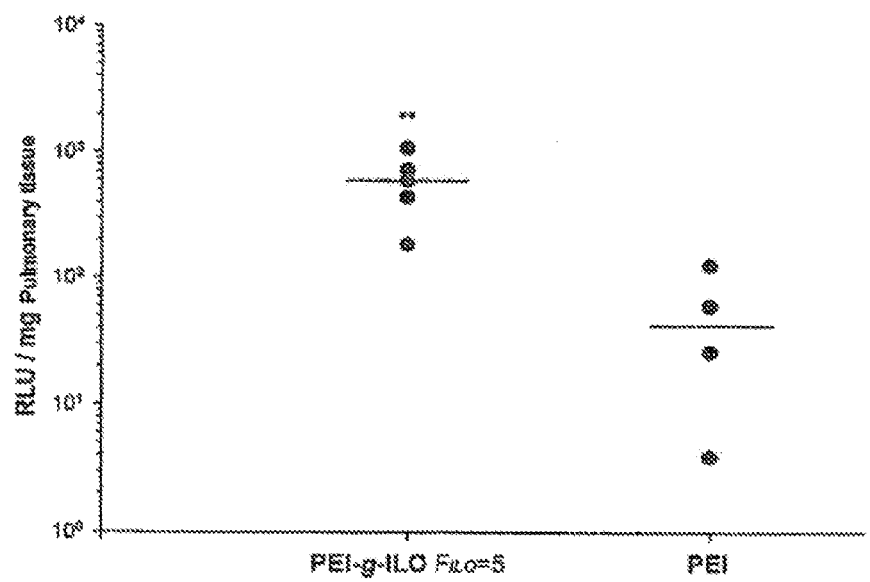
Figure 7A:
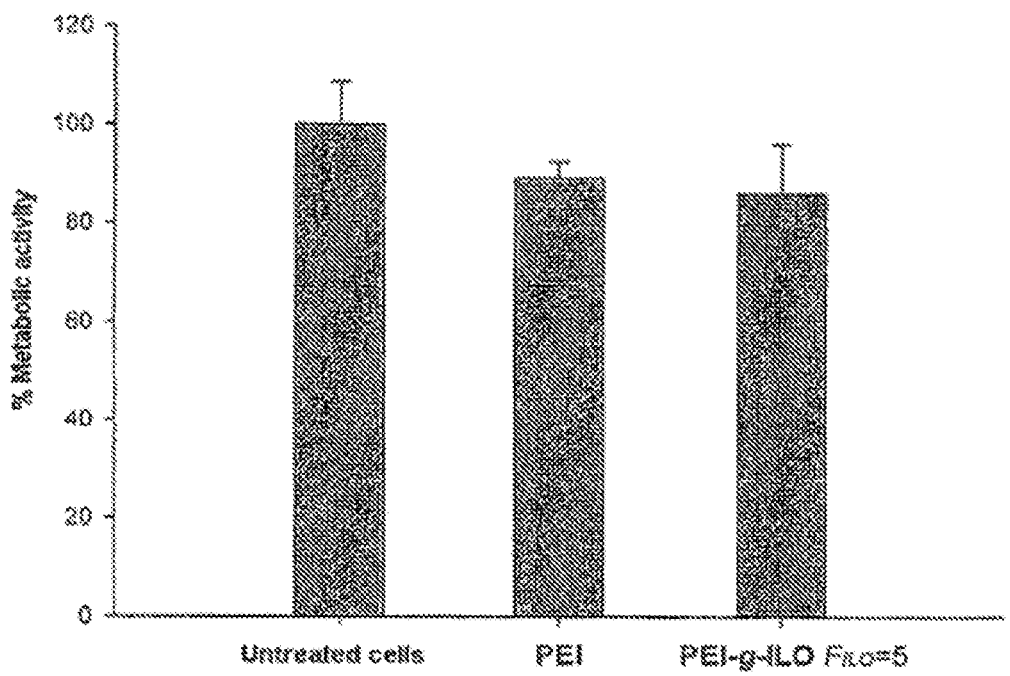
Figure 7B:
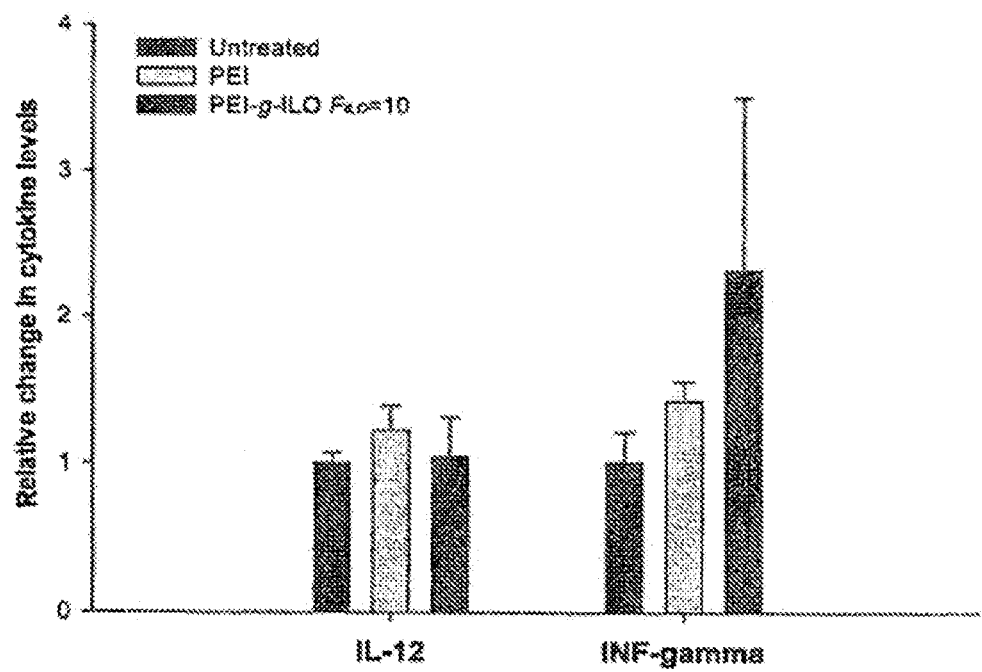

PEI-g-ILO $F_{ILO}$=5 and PEI gene vector particles were delivered to the lungs of BALB/C mice via aerosol, and the gene expression was analyzed 24 h after the gene delivery. The measurement of the luciferase gene expression versus the in-vivo bioluminescence image shows a strong signal in the lungs of mice which have been treated with PEI-g-ILO $F_{ILO}$=5 gene vectors, but reached the detection limit in the case of PEI gene vectors (FIG. 6A). For a quantitative evaluation of the luciferase per mg of pulmonary tissue, the mice were sacrificed and the lungs were isolated. The luciferase expression measured in homogenized pulmonary tissue was significantly 14 times higher for PEI-g-ILO $F_{ILO}$=5 gene vectors than for PEI gene vectors (FIG. 6B).

Toxicity In-Vitro and In-Vivo

The in-vitro viability after application of the gene vector particles (PEI-g-ILO $F_{ILO}$=5/pCMV-luc or PEI/pCMV-luc) was measured using an MTT assay. In comparison with PEI, no increase in cytotoxicity was observed (86.0±10.1% cell viability for PEI-g-ILO $F_{ILO}$=5 in contrast to 89.2±3.2% for PEI). For determining the in-vivo toxicity and the inflammation, serum was obtained from treated mice, and the inflammatory cytokines including interleukin-12 (IL-12) and interferon-γ (INF-γ) were measured. Similarly as in the case of the in-vitro MTT results, no significant increase in the cytokines was detected by ELISA 24 h after the gene delivery.

The above experiments have demonstrated that the prostaglandin-$I_2$ analog ILO, an $IP_1$ receptor agonist, can be used as targeting ligand for improving the gene transfer of cationic polymers, such as PEI, in pulmonary cells in-vitro and in-vivo. It has been found that the conjugates according to the invention, which comprise a prostaglandin-$I_2$ analog as targeting ligand and a cationic polymer as encapsulation for an active substance, allow a significant improvement in gene expression. Thus, the study has demonstrated that the reporter gene expression was significantly increased in human alveolar (A549) and bronchial epithelial cells (16HBE14o-, BEAS-2B); indeed, up to 46-fold. Furthermore, the luciferase activity in the lungs of mice was significantly, in fact 14 times, higher after aerosol treatment than in the case of PEI.

ILO and TRP are agonists of the human $IP_1$ receptor [29]. Both are approved for the treatment of pulmonal arterial hypertension via aerosol inhalation or i.v. application [20, 30, 31]. $IP_1$ receptors are expressed in the lungs of humans and mice [15, 32-34], and $IP_1$ receptor/ligand complexes are internalized into the cell [35, 36]. These properties are exploited in accordance with the invention so as to make available an improved system for introducing agents into lung cells.

The $IP_1$ receptor expression in various types of lung cells was confirmed by Western blot. To characterize the $IP_1$ receptor expression on the cell surface of lung cells in greater detail, fluorescein-labeled BSA conjugates which were coupled either to ILO or to TRP were synthesized. Both constructs were then incubated together with alveolar (A549) and bronchial (16HBE14o-) epithelial cell lines, and the binding to the cells was analyzed by flow cytometry. The results show that $IP_1$ receptors are present on each of the cell lines tested. However, ILO shows a more pronounced cell surface binding than TRP, which is why ILO was used as the targeting ligand in all subsequent experiments. The specificity of the binding of the $IP_1$ receptor was demonstrated by inhibition experiments with the specific $IP_1$ receptor antagonist CAY10449 [27, 28, 32] and by an excess of free ILO.

To confirm these observations, confocal laser scanning microscopy was carried out, and this showed the binding of FLUO-BSA-ILO to the cell surface and the intracellular uptake into 16HBE14o-cells. Therefore, these results confirm that ILO can be used in accordance with the invention as targeting ligand which mediates the binding and intracellular uptake of conjugated substances, such as FLUO-BSA, which is a prerequisite for receptor-mediated uptake of gene vector nanoparticles.

To carry out transfection studies, ILO was conjugated via an amide bond to branched PEI 25 kDa. The synthesis resulted in conjugates with a degree of coupling of $F_{ILO}$=2, 5, 8 and 16. PEI-g-ILO/pCMV-luc particles were screened on 16HBE14o-cells, and the highest transfection efficiency was observed at N/P 4 $F_{ILO}$=5, whereas a higher degree of coupling of from 8 to 16 resulted in a lower transfection rate. This might be due to incomplete release of pCMV-luc at higher degrees of coupling, which was observed using a DNA release assay. The release of pDNA from PEI/p-DNA particles has already been found to be a critical parameter for a successful gene transfer [37]. It can be speculated that an additional hydrophobic interaction of ILO with pDNA might strengthen the pDNA bond. Measuring the size of different particles demonstrated that an increasing amount of ligand results in larger hydrodynamic diameters for PEI-g-ILO/pCMV-luc particles of up to 1 μm. Similar results were obtained by Elfinger et al. when clenbuterol was coupled to PEI [13]. Particles with PEI-g-ILO $F_{ILO}$=5 had hydrodynamic diameters of less than 100 nm. Particles of a similar size were internalized more efficiently than larger particles, which had already been demonstrated [38]. The transfection of alveolar (A549) and bronchial (16HBE14o-, BEAS-2B) epithelial cells with PEI-g-ILO $F_{ILO}$=5/pCMV-luc particles with N/P 4 resulted in a 46-fold increase in the reporter gene expression in comparison with PEI/pCMV-luc particles with the same N/P ratio in all tested cell lines. The improved gene expression which was observed did not result in a greater increase in the metabolic toxicity, as measured in an MTT assay. Furthermore, the hypothesis of the receptor-mediated gene transfer was supported further by the experiments with an inhibition, in 16HBE14o-cells, which was mediated by specific antagonists. The addition of CAY10449 reduced the gene expression to an extent which is comparable to PEI.

A CpG-free luciferase expression plasmid (pCpG-luc) was used for animal experiments. It has emerged that CpG-free plasmids have a less pronounced inflammatory effect than CpG-containing plasmids. It was also demonstrated that they lead to higher and more sustained gene expression in the lungs [39]. Before the animal experiments, PEI-g-ILO $F_{ILO}$=5/pCpG-luc and PEI/pCpG-luc gene vectors were nebulized and various fractions were collected (nebulized, non-nebulized), to test the stability of the particles. Both the gel retardation assay and the particle size measurements revealed no change in the particles after nebulization in comparison to non-nebulized particles. These observations confirm that aerosol formation had no negative effect on the particles. The same results have already been reported [40]. After the aerosol administration to the lungs of mice, the gene expression was significantly, 14 times, higher for PEI-g-ILO $F_{ILO}$=5/pCpG-luc than for PEI/pCpG-luc gene vectors. The measurement of interleukin-12 (IL-12) and interferon-γ (INF-γ) in the mass serum revealed no significant increase in these cytokines. This observation tallies with Gautham et al.

[41], who demonstrated that the aerosol administration of PEI-DNA particles does not induce a higher cytokine response.

In summary, it can be said that a novel target-finding structure for delivering substances into the lungs is provided in accordance with the invention. The potential of prostacyclin analogs and in particular of ILO as the ligand for targeting purposes was recognized by the inventors and exploited as a "ferry" for the administration of substances into pulmonary cells. In particular, ILO prostacyclin analogs are useful as targeting ligands for nonviral vectors in aerosol form. Using fluorescein-based molecular conjugates, it was demonstrated that the $IP_1$ receptor is a suitable candidate for a receptor-mediated gene transfer in pulmonary cells. The receptor-specific binding and uptake of molecule conjugates was demonstrated not only for alveolar cells, but also for bronchial epithelial cells and Clara cells. The conjugates according to the invention result in a specific significant increase in gene expression in-vitro and in-vivo. The more than 10-fold increase in gene expression makes it possible to reduce the amount of pDNA and of gene carrier, which reduces the DNA- or carrier-mediated toxicity and inflammation.

The results of this example are shown in FIGS. 1 to 7 and Table 1:

Table 1: Physical characterization of PEI/pCMV-luc and PEI-g-ILO/pCMV-luc gene vectors using PEI-g-ILO with different degrees of coupling ($F_{ILO}$=2, 5, 8, 16) at different N/P ratios:

Measurements of the particle size and the polydispersity (in parentheses). The results are shown as the mean±standard deviation (n=3).

FIG. 1

The Western blot shows the expression of $IP_1$ receptor protein with 67 kDa in human alveolar (A549) and bronchial (BEAS-2B, 16HBE14o-) epithelial cells. Each lane was loaded with 40 µg of protein extract.

FIG. 2

Targeting the $IP_1$ receptor with TRP and ILO to alveolar (A549) and bronchial (16HBE14o-) epithelial cell lines. The incubation of FLUO-BSA, FLUO-BSA-TRP and FLUO-BSA-ILO was performed at a concentration of 0.5 µM (n=4): FACS measurements. The results are shown as the mean±standard deviation. ** means statistical significance at p<0.01.

FIG. 3

Distribution of $IP_1$ receptor and the receptor binding in alveolar (A549), bronchoalveolar (H441) and bronchial (16HBE14o-, BEAS-2B) epithelial cells. The incubation with FLUO-BSA-ILO and FLUO-BSA was performed at a concentration of 0.5 µM (n=4): FACS measurements (a). 16HBE14o-(b,c) and A549 (d) cells were incubated with 25 nM FLUO-BSA-ILO and FLUO-BSA together with increasing concentrations of CAY10449 (n=4); FACS measurements (b,c,d). For the confocal laser scanning microscopy, 16HBE14o-cells were incubated with 0.5 µM FLUO-BSA-ILO and FLUO-BSA (e). The results are shown as the mean±standard deviation. ** means statistical significance at p<0.01.

FIG. 4

DNA retardation assay for PEI and different PEI-g-ILO constructs with N/P=4. Polymers complexed with pCMV-luc were incubated with (+) and without (−) heparan sulfate, separated on agarose gel and visualized under UV light after staining with ethidium bromide.

FIG. 5

Transfection efficiency in-vitro. The transfection of 16HBE14o-cells with pCMV-luc complexed with various PEI-g-ILO constructs of different N/P ratios (n=4): measurement of the luciferase gene expression (a), inhibition experiment of PEI/pCMV-luc and PEI-g-ILO $F_{ILO}$=5/pCMV-luc particles with an N/P ratio of 4 with CAY10449 (n=3): measurement of the luciferase gene expression (b). Transfection of A549, 16HBE14o- and BEAS-2B with PEI/pCMV-luc and PEI-g-ILO $F_{ILO}$=5/pCMV-luc with an N/P ratio of 4 (n=6): measurement of the luciferase gene expression (c). The luciferase gene expression was measured as luminescence in relative light units (RLU) during 10 s/mg cellular protein. The results are shown as the mean±standard deviation. ** means statistical significance at p<0.01.

FIG. 6

In-vivo luciferase gene expression obtained with PEI/pCpG-luc and PEI-g-ILO $F_{ILO}$=5/pCpG-luc particles with an N/P ratio=4 in lungs of BALB/c mice after aerosol administration (n=5). Bioluminescence images with an exposure time of 10 min after 24 h (a). Luciferase expression measurement in lung homogenates of mice with an exposure time of 30 s was performed 24 h after the transfection (b). The results are shown as the vertical point with median. ** means statistical significance at p<0.01.

FIG. 7

In comparison with PEI-g-ILO $F_{ILO}$=5/pCMV-luc particles and in comparison with untreated cells, the transfection of alveolar (A549) and bronchial (16HBE14o-, BEAS-2B) epithelial cells with PEI/pCMV-luc particles with N/P=4 did not result in an increase in the metabolic toxicity as measured in an MTT assay (a). Furthermore, interleukin-12 (IL-12) and interferon-γ (IFN-γ) were measured in mouse serum after the delivery of PEI-g-ILO $F_{ILO}$=10 to the lungs of mice in comparison with the delivery of PEI and untreated mice. No significant increase in these cytokines was observed.

EXAMPLE 2

Dose-Dependent Gene Vector Targeting in Pulmonary Cells

16HBE14o-cells were transfected with PEI and PEI-g-ILO gene vector particles by reducing the amount of pCMV-luc from 1 µg to 0.25 µg (FIG. 8). 24 h after the transfection, the gene transfer efficiency decreased in a dose-dependent manner. The highest degree of gene expression was found with 1 µg of pCMV-luc. 0.5 µg of pCMV-luc complexed with PEI-g-ILO $F_{ILO}$=5, however, resulted in an expression identical to 1 µg of pCMV-luc complexed with unmodified PEI ($3.3*10^5$ versus $3.2*10^5$ RLU/10 s/mg protein).

To demonstrate that the gene transfer efficiency decreases in a dose-dependent manner, a transfection experiment was carried out in which the amount of gene vector particles was reduced. This demonstrated that the reduction of PEI-g-ILO $F_{ILO}$=5 gene vector particles down to 50% results in the same expression in comparison with 100% PEI gene vector particles. These data demonstrate clearly that the amount of pDNA and gene carrier can be reduced while maintaining the same degree of expression. Furthermore, it is also possible to reduce both pDNA and the carrier-mediated toxicity and inflammation.

Figures 8, 9:
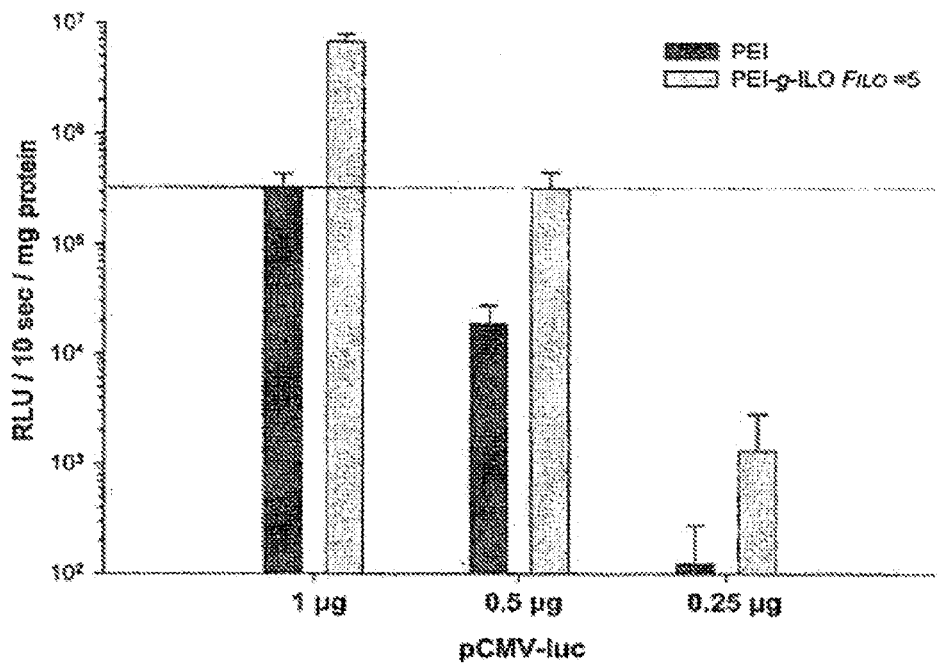

The results of this example are also shown in FIG. 8.

The references which are referred to in the description are specified hereinbelow.

1. Gill D R, Davies L A, Pringle I A, Hyde S C. The development of gene therapy for diseases of the lung. Cell Mol. Life. Sci. 2004 February; 61(3):355-68.

2. Gurunathan S, Klinman D M, Seder R A. DNA vaccines: immunology, application, and optimization*. Annu. Rev. Immunol. 2000; 18:927-74.
3. Davies L, Hyde, C and Gill, D R Plasmid inhalation: delivery to the airways; 2005.
4. Rudolph C, Schillinger U, Ortiz A, Plank C, Golas M M, Sander B, et al. Aerosolized nanogram quantities of plasmid DNA mediate highly efficient gene delivery to mouse airway epithelium. Mol. Ther. 2005 September; 12(3):493-501.
5. Canonico A E, Conary J T, Meyrick B O, Brigham K L. Aerosol and intravenous transfection of human alpha 1-antitrypsin gene to lungs of rabbits. Am. J. Respir. Cell Mol. Biol. 1994 January; 10(1):24-9.
6. McLachlan G, Baker A, Tennant P, Gordon C, Vrettou C, Renwick L, et al. Optimizing aerosol gene delivery and expression in the ovine lung. Mol. Ther. 2007 February; 15(2):348-54.
7. Alton E W, Stem M, Farley R, Jaffe A, Chadwick S L, Phillips J, et al. Cationic lipid-mediated CFTR gene transfer to the lungs and nose of patients with cystic fibrosis: a double-blind placebo-controlled trial. Lancet. 1999 Mar. 20; 353(9157):947-54.
8. Boussif O, Lezoualc'h F, Zanta M A, Mergny M D, Scherman D, Demeneix B, et al. A versatile vector for gene and oligonucleotide transfer into cells in culture and in vivo: polyethylenimine. Proc. Natl. Acad. Sci. USA. 1995 Aug. 1; 92(16):7297-301.
9. Dunlap D D, Maggi A, Soria M R, Monaco L. Nanoscopic structure of DNA condensed for gene delivery. Nucleic Acids Res. 1997 Aug. 1; 25(15):3095-101.
10. Kircheis R, Kichler A, Wallner G, Kursa M, Ogris M, Felzmann T, et al. Coupling of cell-binding ligands to polyethylenimine for targeted gene delivery. Gene Ther. 1997 May; 4(5):409-18.
11. Chul Cho K, Hoon Jeong J, Jung Chung H, Joe C O, Wan Kim S, Gwan Park T. Folate receptor-mediated intracellular delivery of recombinant caspase-3 for inducing apoptosis. J. Control. Release. 2005 Nov. 2; 108(1):121-31.
12. Elfinger M, Maucksch C, Rudolph C. Characterization of lactoferrin as a targeting ligand for nonviral gene delivery to airway epithelial cells. Biomaterials. 2007 August; 28(23):3448-55.
13. Elfinger M, Geiger J, Hasenpusch G, Uzgun S, Sieverling N, Aneja M K, et al. Targeting of the beta(2)-adrenoceptor increases nonviral gene delivery to pulmonary epithelial cells in vitro and lungs in vivo. J. Control. Release. 2009 May 5; 135(3):234-41.
14. Blessing T, Kursa M, Holzhauser R, Kircheis R, Wagner E. Different strategies for formation of pegylated EGF-conjugated PEI/DNA complexes for targeted gene delivery. Bioconjug. Chem. 2001 July-August; 12(4):529-37.
15. Coleman R A, Smith W L, Narumiya S. International Union of Pharmacology classification of prostanoid receptors: properties, distribution, and structure of the receptors and their subtypes. Pharmacol. Rev. 1994 June; 46(2):205-29.
16. Narumiya S, Sugimoto Y, Ushikubi F. Prostanoid receptors: structures, properties, and functions. Physiol. Rev. 1999 October; 79(4):1193-226.
17. Stitham J, Arehart E J, Gleim S R, Douville K L, Hwa J. Human prostacyclin receptor structure and function from naturally-occurring and synthetic mutations. Prostaglandins Other Lipid Mediat. 2007 January; 82 (1-4):95-108.
18. Clark R B, Knoll B J, Barber R. Partial agonists and G protein-coupled receptor desensitization. Trends Pharmacol. Sci. 1999 July; 20(7):279-86.
19. Ferguson S S. Evolving concepts in G protein-coupled receptor endocytosis: the role in receptor desensitization and signaling. Pharmacol. Rev. 2001 March; 53(1):1-24.
20. Strauss W L, Edelman J D. Prostanoid therapy for pulmonary arterial hypertension. Clin. Chest. Med. 2007 March; 28(1):127-42; ix.
21. Snyder S L, Sobocinski P Z. An improved 2,4,6-trinitrobenzenesulfonic acid method for the determination of amines. Anal. Biochem. 1975 March; 64(1):284-8.
22. Ungaro F, De Rosa G, Miro A, Quaglia F. Spectrophotometric determination of polyethylenimine in the presence of an oligonucleotide for the characterization of controlled release formulations. J. Pharm. Biomed. Anal. 2003 Feb. 5; 31(1):143-9.
23. Huth S, Lausier J, Gersting S W, Rudolph C, Plank C, Welsch U, et al. Insights into the mechanism of magnetofection using PEI-based magnetofectins for gene transfer. J. Gene Med. 2004 August; 6(8):923-36.
24. Rudolph C, Ortiz A, Schillinger U, Jauernig J, Plank C, Rosenecker J. Methodological optimization of polyethylenimine (PEI)-based gene delivery to the lungs of mice via aerosol application. J. Gene Med. 2005 January; 7(1):59-66.
25. Buckley S M, Howe S J, Rahim A A, Buning H, McIntosh J, Wong S P, et al. Luciferin detection after intranasal vector delivery is improved by intranasal rather than intraperitoneal luciferin administration. Hum. Gene Ther. 2008 October; 19(10):1050-6.
26. Zhang Z, Austin S C, Smyth E M. Glycosylation of the human prostacyclin receptor: role in ligand binding and signal transduction. Mol. Pharmacol. 2001 September; 60(3):480-7.
27. Bley K R, Bhattacharya A, Daniels D V, Gever J, Jahangir A, O'Yang C, et al. RO1138452 and RO3244794: characterization of structurally distinct, potent and selective IP (prostacyclin) receptor antagonists. Br. J. Pharmacol. 2006 February; 147(3):335-45.
28. Clark R D, Jahangir A, Severance D, Salazar R, Chang T, Chang D, et al. Discovery and SAR development of 2-(phenylamino) imidazolines as prostacyclin receptor antagonists [corrected]. Bioorg. Med. Chem. Lett. 2004 Feb. 23; 14(4):1053-6.
29. Olschewski H, Rose F, Schermuly R, Ghofrani H A, Enke B, Olschewski A, et al. prostacyclin and its analogues in the treatment of pulmonary hypertension. Pharmacol. Ther. 2004 May; 102(2):139-53.
30. Skoro-Sajer N, Lang I. Treprostinil for the treatment of pulmonary hypertension. Expert Opin. Pharmacother. 2008 June; 9(8):1415-20.
31. Krug S, Sablotzki A, Hammerschmidt S, Wirtz H, Seyfarth H J. Inhaled iloprost for the control of pulmonary hypertension. Vasc. Health Risk Manag. 2009; 5(1):465-74.
32. Ayer L M, Wilson S M, Traves S L, Proud D, Giembycz M A. 4,5-Dihydro-1H-imidazol-2-yl)-[4-(4-isopropoxy-benzyl)-phenyl]-amine (RO1138452) is a selective, pseudo-irreversible orthosteric antagonist at the prostacyclin (IP)-receptor expressed by human airway epithelial cells: IP-receptor-mediated inhibition of CXCL9 and CXCL10 release. J. Pharmacol. Exp. Ther. 2008 February; 324(2):815-26.
33. Boie Y, Rushmore T H, Darmon-Goodwin A, Grygorczyk R, Slipetz D M, Metters K M, et al. Cloning and expression of a cDNA for the human prostanoid IP receptor. J. Biol. Chem. 1994 Apr. 22; 269(16):12173-8.
34. Namba T, Oida H, Sugimoto Y, Kakizuka A, Negishi M, Ichikawa A, et al. cDNA cloning of a mouse prostacyclin receptor. Multiple signaling pathways and expression in thymic medulla. J. Biol. Chem. 1994 Apr. 1; 269(13):9986-92.
35. Giovanazzi S, Accomazzo M R, Letari O, Oliva D, Nicosia S. Internalization and down-regulation of the prostacyclin receptor in human platelets. Biochem. J. 1997 Jul. 1; 325 (Pt 1):71-7.
36. Smyth E M, Austin S C, Reilly M P, FitzGerald G A. Internalization and sequestration of the human prostacyclin receptor. J. Biol. Chem. 2000 Oct. 13; 275(41):32037-45.
37. Huth S, Hoffmann F, von Gersdorff K, Laner A, Reinhardt D, Rosenecker J, et al. Interaction of polyamine gene vectors with RNA leads to the dissociation of plasmid DNA-carrier complexes. J. Gene Med. 2006 December; 8(12): 1416-24.
38. Rejman J, Oberle V, Zuhorn I S, Hoekstra D. Size-dependent internalization of particles via the pathways of clathrin- and caveolae-mediated endocytosis. Biochem. J. 2004 Jan. 1; 377 (Pt 1):159-69.
39. Hyde S C, Pringle I A, Abdullah S, Lawton A E, Davies L A, Varathalingam A, et al. CpG-free plasmids confer reduced inflammation and sustained pulmonary gene expression. Nat. Biotechnol. 2008 May; 26(5):549-51.
40. Rudolph C, Muller R H, Rosenecker J. Jet nebulization of PEI/DNA polyplexes: physical stability and in vitro gene delivery efficiency. J. Gene Med. 2002 January-February; 4(1):66-74.
41. Gautam A, Densmore C L, Waldrep J C. Pulmonary cytokine responses associated with PEI-DNA aerosol gene therapy. Gene Ther. 2001 February; 8(3):254-7.

We claim:

1. A conjugate of agent complex and at least one target-finding ligand, where the agent complex comprises a nanoparticle or nanocapsule comprising an agent encapsulated with biodegradable polyetheleneimine polymer encapsulation material and the target-finding ligand is iloprost or treprostinil, and wherein the target-finding ligand is not the agent.

2. The conjugate as claimed in claim 1 wherein the agent is a nucleic acid or a derivative thereof, a peptide, polypeptide or derivative thereof, an active substance or a tracer.

3. The conjugate as claimed in claim 2, characterized in that the nucleic acid is a DNA or RNA whose lack or deficiency causes a disease or is a DNA or RNA which encodes a polypeptide whose lack or deficiency causes a disease or which has an immunomodulatory activity.

4. The conjugate as claimed in claim 2, characterized in that the agent is a peptide or polypeptide whose lack or deficiency causes a disease or which has an immunomodulatory activity.

5. The conjugate of claim 1, wherein the agent is a product which compensates for a protein defect or lack of protein and is nucleic acid, protein, protein derivative or protein fragment or a pharmaceutical which is active in the lungs or a mixture thereof.

6. The conjugate as claimed in claim 2, characterized in that the active substance is an anti-inflammatory active substance or a steroid.

7. The conjugate of claim 1, wherein the agent is a reporter molecule.

8. The conjugate of claim 1, wherein an agent complex of encapsulation material and nucleic acid is additionally pegylated.

9. A method for treatment of a pulmonary disease caused by a protein or a genetic defect, comprising administering to a subject in need thereof the conjugate of an agent complex and at least one target-finding ligand of claim 1.

10. The conjugate of claim 2, wherein a ratio of polymer to nucleic acid measured as the molar ratio of polymer nitrogen content to DNA phosphate content is in a range of from 10:1 to 1:20.

11. A method of treatment of pulmonary diseases, comprising administering to a subject in need thereof an effective amount of the conjugate of an agent complex and at least one target-finding ligand of claim 1.

12. The conjugate of claim 1, further comprising customary pharmaceutical adjuvants in a form suitable for inhalation.

13. The conjugate of claim 7, wherein the reporter molecule is a radioactive or fluorescent tracer.

14. The method of claim 9, wherein the pulmonary disease is cystic fibrosis.

* * * * *